(12) United States Patent
   Shor et al.

(10) Patent No.: US 12,653,447 B2
(45) Date of Patent: Jun. 16, 2026

(54) PERSONAL UNIVERSAL DENDROGRAMIC HOLOGRAPHIC SIGNATURE FROM EEG DATA ANALYSIS FOR DIAGNOSIS OF NEURO-PSYCHIATRIC DISEASES

(71) Applicants: Ramot at Tel-Aviv University Ltd., Tel-Aviv (IL); Mor Research Applications Ltd., Ramat Gan (IL)

(72) Inventors: Oded Shor, Tel-Aviv (IL); Felix Benninger, Tel-Aviv (IL); Andrei Khrennikov, Tel-Aviv (IL)

(73) Assignees: Ramot at Tel-Aviv University Ltd., Tel-Aviv (IL); Mor Research Applications Ltd., Ramat Gan (IL)

( * ) Notice: Subject to any disclaimer, the term of this patent is extended or adjusted under 35 U.S.C. 154(b) by 0 days.

(21) Appl. No.: 18/846,301

(22) PCT Filed: Mar. 10, 2023

(86) PCT No.: PCT/IL2023/050252
   § 371 (c)(1),
   (2) Date: Sep. 12, 2024

(87) PCT Pub. No.: WO2023/175602
   PCT Pub. Date: Sep. 21, 2023

(65) Prior Publication Data
   US 2025/0107745 A1     Apr. 3, 2025

Related U.S. Application Data

(60) Provisional application No. 63/319,416, filed on Mar. 14, 2022.

(51) Int. Cl.
   *A61B 5/00*     (2006.01)
   *A61B 5/374*     (2021.01)

(52) U.S. Cl.
   CPC ............ *A61B 5/4088* (2013.01); *A61B 5/374* (2021.01); *A61B 5/7264* (2013.01)

(58) Field of Classification Search
   None
   See application file for complete search history.

(56) References Cited

U.S. PATENT DOCUMENTS

2015/0088024 A1* 3/2015 Sackellares ............ A61B 5/291
                                                            600/544
2017/0340262 A1* 11/2017 Momose .............. A61B 5/4088
                          (Continued)

FOREIGN PATENT DOCUMENTS

WO     WO 2022/064501     3/2022
WO     WO 2023/175602     9/2023

OTHER PUBLICATIONS

International Search Report and the Written Opinion Dated Jun. 25, 2023 From the International Searching Authority Re. Application No. PCT/IL2023/050252. (11 Pages).
                          (Continued)

*Primary Examiner* — Eric J Messersmith
*Assistant Examiner* — Matthew Eric Ogles

(57)                ABSTRACT
There is provided a method of diagnosing a medical state associated with a neuro-psychiatric disorder in a subject, comprising: receiving EEG datasets from EEG electrodes monitoring a head of the subject, computing events for the EEG datasets, clustering the events into clusters, computing a p-adic representation of the clusters, extracting a p-adic topology from the p-adic representation of the clusters, computing a personal universal dendrogramic holographic signature (PUDHS) of the p-acid topology relative to a personalized threshold that separates between a relative large distance between events and a relatively small distance between events, the PUDHS denoting number of events below the personalized threshold, and diagnosing the medi-
                          (Continued)

cal state associated with the neuro-psychiatric disorder according to the PUDHS relative to a medical threshold that separates between presence of the medical state and non-presence of the medical state.

16 Claims, 21 Drawing Sheets

(56) References Cited

U.S. PATENT DOCUMENTS

| | | | | |
|---|---|---|---|---|
| 2018/0345006 | A1* | 12/2018 | Ambrose | A61B 5/0536 |
| 2019/0059762 | A1* | 2/2019 | Starr | G16H 40/63 |
| 2019/0269348 | A1* | 9/2019 | Medvedovsky | A61B 5/7235 |
| 2020/0237247 | A1* | 7/2020 | Glik | A61B 5/369 |
| 2020/0260977 | A1* | 8/2020 | Kang | G16H 50/50 |

OTHER PUBLICATIONS

Albeverio et al. "Memory Retrieval as a P-Adic Dynamical System", Biosystems, 49(2): 105-115, Feb. 1, 1999.
Arns et al. "Quantitative EEG (QEEG) in Psychiatry: Diagnostic or Prognostic Use?", Clinical Neurophysiology, 25(8):1504-1506, Aug. 2014.
Asano et al. "Quantum Adaptivity in Biology: From Genetics to Cognition", Book, 185 P., 2015.
Baradits et al. "Alterations in Resting-State Gamma Activity in Patients with Schizophrenia: A High-Density EEG Study", European Archives of Psychiatry and Clinical Neuroscience, 269:429-437, Mar. 22, 2018.
Barbour et al. "Extremal Variety as the Foundation of a Cosmological Quantum, High Energy Physics—Theoryheory", eprint arXiv:hep-th/9203041: 1-35, Mar. 1992.
Birur et al. "Brain Structure, Function, and Neurochemistry in Schizophrenia and Bipolar Disorder—A Systematic Review of the Magnetic Resonance Neuroimaging Literature", Npj Schizofrenia, 3(15): 1-15, Apr. 3, 2017.
Bohm et al. "The Undivided Universe: An Ontological Interpretation of Quantum Theory", 47P, 1993.
Cervenka et al. "Epilepsy", Seminars in Neurology, 36(4): 342-349, 2016.
Collins et al. "Grand Challenges in Global Mental Health: Integration in Research, Policy, and Practice", Plos Medicine, 10(4):e1001434: 1-6, Apr. 30, 2013.
Dragovich et al. "A P-Adic Model of DNA Sequence and Genetic Code", P-Adic Numbers, Ultrametric Analysis, and Applications, 1: 34-41 , Feb. 8, 2009.
Dragovich et al. "P-Adic Mathematical Physics: the Fsrst 30 Years", p-Adic Numbers, Ultrametric Analysis and Applications, 9(2): 87-121, May 19, 2017.
Dragovich et al. "P-Adic Mathematics and Theoretical Biology", Bio Systems, 199(1): 104288-1-104288-22, Nov. 12, 2020.
Dragovich et al. "Ultrametrics in the Genetic Code and the Genome", Applied Mathematics and Computation, 309: 350-358, Sep. 15, 2017.
Dubischar et al. "Ap-Adic Model for the Process of Thinking Disturbed by Physiological and Information Noise", Journal of Theoretical Biology, 197(4): 451-467, Apr. 21, 1999.
Endres et al. "Electroencephalographic Findings in Schizophreniform and Affective Disorders", International Journal of Psychiatry in Clinical Practice, 20(3): 157-164,May 16, 2016.
García-Compeán et al. "P-Adic Open String Amplitudes With Chan-Paton Factors Coupled to A Constant B-Field", Nuclear Physics B, 951: 114904-1-114904-34, Feb. 2020.
Johnson "Information Theory in Biology After 18 Years: Information Theory Must Be Modified for the Description of Living Things", Science, 168(3939): 1545-1550, Jun. 26, 1970.

Keinejad et al. "WHO Mental Health Gap Action Programme (MhGAP) Intervention Guide: A Systematic Review of Evidence From Low and Middle-Income Countries", Evid Based Ment Health, 21(1): 30-34, Feb. 2018.
Kennis et al. "Prospective Biomarkers of Major Depressive Disorder: A Systematic Review and Meta-Analysis", Molecular Psychiatry, 25: 321-338, Nov. 19, 2019.
Khrennikov "Human Subconscious as Ap-Adic Dynamical System", Journal of Theoretical Biology, 193(2): 179-196, Jul. 21, 1998.
Khrennikov "Non-Archimedean Analysis", Non-Archimedean Analysis: Quantum Paradoxes, Dynamical Systems and Biological Models, 427: 101-129, 1997.
Khrennikov "Replica Symmetry Breaking Related to a General Ultrametric Space I: Replica Matrices and Functionals", Physica A: Statistical Mechanics and Its Applications, 359: 222-240, Jan. 1, 2006.
Livingston et al. "Dementia Prevention, Intervention and Care", The Lancet, 390(10113): 2673-2734, Jul. 19, 2017.
Malhi et al. "Depression", The Lancet, 392(10161): 2290-2312, Published Online Nov. 2, 2018.
Maran et al. "Electrophysiological Insights Into Connectivity Anomalies in Schizophrenia: A Systematic Review", Neuropsychiatric Electrophysiology, 2(Art.6): 1-9, Nov. 5, 2016.
Newson et al. "EEG Frequency Bands in Psychiatric Disorders: A Review of Resting State Studies", Frontiers in Human Neuroscience, 12: 521-1-521-24, Jan. 9, 2019.I.
Oh et al. "Deep Convolutional Neural Network Model for Automated Diagnosis of Schizophrenia Using EEG Signals", Applied Sciences, 9(14): 2870-1-2870-14, Published Online Jul. 18, 2019.
Olbrich et al. "EEG Biomarkers in Major Depressive Disorder: Discriminative Power and Prediction of Treatment Response", International Review of Psychiatry, 25(5): 604-618, Oct. 23, 2013.
Owen et al. "Schizophrenia", The Lancet, 388(10039): 86-97, Published Online Jan. 14, 2016.
Parisi "A Sequence of Approximated Solutions to the S-K Model for Spin Glasses", Journal of Physics A: Mathematical and General, 13(4): 115-121, Jan. 4, 1980.
Parisi "Infinite Number of Order Parameters for Spin-Glasses", Physical Review Letters, 43(23): 1754-1756, Dec. 3, 1979.
Parisi "On P-Acid Functional Integrals", Modern Physics Letters A, 3(6): 639-643, 1988.
Parisi "P-adic Numbers and Replica Symmetry Breaking", The European Physical Journal B—Condensed Matter and Complex Systems, 14(3): 535-542, Mar. 2000.
Parisi "The Order Parameter for Spin Glasses: A Function on the Interval 0-1", Journal of Physics A: Mathematical and General, 13(3): 1101-1112, Jul. 31, 1979.
Shor et al. "Dendrogramic Representation of Data: CHSH Violation Vs. Nonergodicity", Entropy, 23(8): 971-1-971-21, Jul. 28, 2021.
Shor et al. "EEG P-Adic Quantum Potential Accurately Identifies Depression, Schizophrenia and Cognitive Decline", PLoS ONE, 16(8): e0255529-1-e0255529-19, Aug. 5, 2021.
Shor et al. "Representation of the Universe as a Dendrogramic Hologram Endowed With Relational Interpretation", Entropy, 23(5): 584-1-584-15, May 8, 2021.
Smith "EEG in the Diagnosis, Classification, and Management of Patients With Epilepsy", Journal of Neurology, Neurosurgery and Psychiatry, 76(Suppl 2): ii2-ii7, Jun. 2005.
Smolin "The Dynamics of Difference" , Foundations of Physics, 48(2): 121-134, Feb. 8, 2018.
Strawbridge et al. "Biomarkers for Depression: Recent Insights, Current Challenges and Future Prospects", Neuropsychiatric Disease and Treatment, 13: 1245-1262, May 10, 2017.
Volovich "P-Adic String", Classical Quantum Gravity, 4(4): L83-L87, Jul. 1, 1987.
Wade et al. "Using Electroencephalography for Treatment Guidance in Major Depressive Disorder", Biological Psychiatry: Cognitive Neuroscience and Neuroimaging, 1(5): 411-422, Sep. 2016.
Wu et al. "An Electroencephalographic Signature Predicts Antidepressant Response in Major Depression", Nature Biotechnology, 38(4): 439-447, Feb. 10, 2020.

(56)     References Cited

OTHER PUBLICATIONS

Wu et al. "Depression Detection Using Relative EEG Power Induced by Emotionally Positive Images and a Conformal Kernel Support Vector Machine", Applied Sciences. 8(8): 1244-1-1244-18, Jul. 27, 2018.
Zelenov "Entropy Gain in P-Adic Quantum Channels", Physics of Particles and Nuclei, 51(4): 485-488, Sep. 2020.
Zhuo et al. "The Rise and Fall of MRI Studies in Major Depressive Disorder", Translational Psychiatry, 9(1): 335-1-335-14, Dec. 9, 2019.
International Preliminary Report on Patentability Dated Sep. 26, 2024 From the International Bureau of WIPO Re. Application No. PCT/IL2023/050252. (8 Pages).

* cited by examiner

200

The result is agglomerative hierarchical cluster tree,
returned as a numeric matrix Z which is an (n*b -1)-by-3 matrix, where
n*b = number of rows of H (number of row vectors).

Each leaf node of the agglomerative hierarchical cluster binary tree has a path
from root to leaf. The leaf path passes m nodes of bifurcations.
Each node of bifurcation, in a leaf path, bifurcates right or left. Thus, each leaf
path will be represented as a binary string, *branch$_r$, r ∈ 1,2.. n n = number of rows
in matrix H*. The i'th ( $i$ ∈ 1,2..*m*) position of the binary string will have the value 1
if at the i'th node of bifurcation ( $i$ ∈ 1,2..*m*) the path bifurcates right.
The i'th ( $i$ ∈ 1,2..*m*) position of the binary string will have the value 0 if at the i'th
node of bifurcation ( $i$ ∈ 1,2..*m*) the path bifurcates left.

All *branch$_r$* will be joind to form a matrix D, which represents the p-adic scale free
dendrogram with *n* number of rows and *w* number of columns where
$$n = number\ of\ discrete\ locations$$
$$w = maximal\ i\text{'}th\ in\ all\ path,\ with\ the\ value\ 1$$
Each *branch$_r$* i'th position that is bigger than its *m* but smaller or equal to *w* is filled
with the value 0. Each row in the D matrix which presents a p-adic scale free
dendrogram is a string with values of 0/1. Each such row represents the j'th leaf
node branch of the p-adic scale free dendrogram, *where j* ∈ 1,2.. n n = number of
rows in matrix H*.

For each row in D, which represent the *j'th* leaf node *branch*, we calculated
the sum of p-adic expansion as follows.
$$branch_j = (a_1, a_2, a_3 ... a_k)\ where\ a_1 ∈ 0,1\ thus\ V_j = \sum_{i-1}^{w} a_1 2^{4-1}$$
Thus, $V_j$ uniquely represents the p-adic scale free *branch* of the *j'th* last node.

Calculate:
$$maximal\ p\text{-}adic\ ball\ of\ dendrogram = [log_2(max\ V_j\ of\ dendrogram))]$$
Choose natural number z
$$T_{personal\ Universal\ dendrogram} = 2^{maximal\ p\text{-}adic\ ball\ of\ dendrogram-z}$$
$$PUDHS = number\ of\ edges\ V_j\ which\ are\ smaller\ than\ T_{personal\ Universal\ dendrogram}$$

FIG. 4 continued

Machine learning for
choosing best z, m, b values

FIG. 6 continued

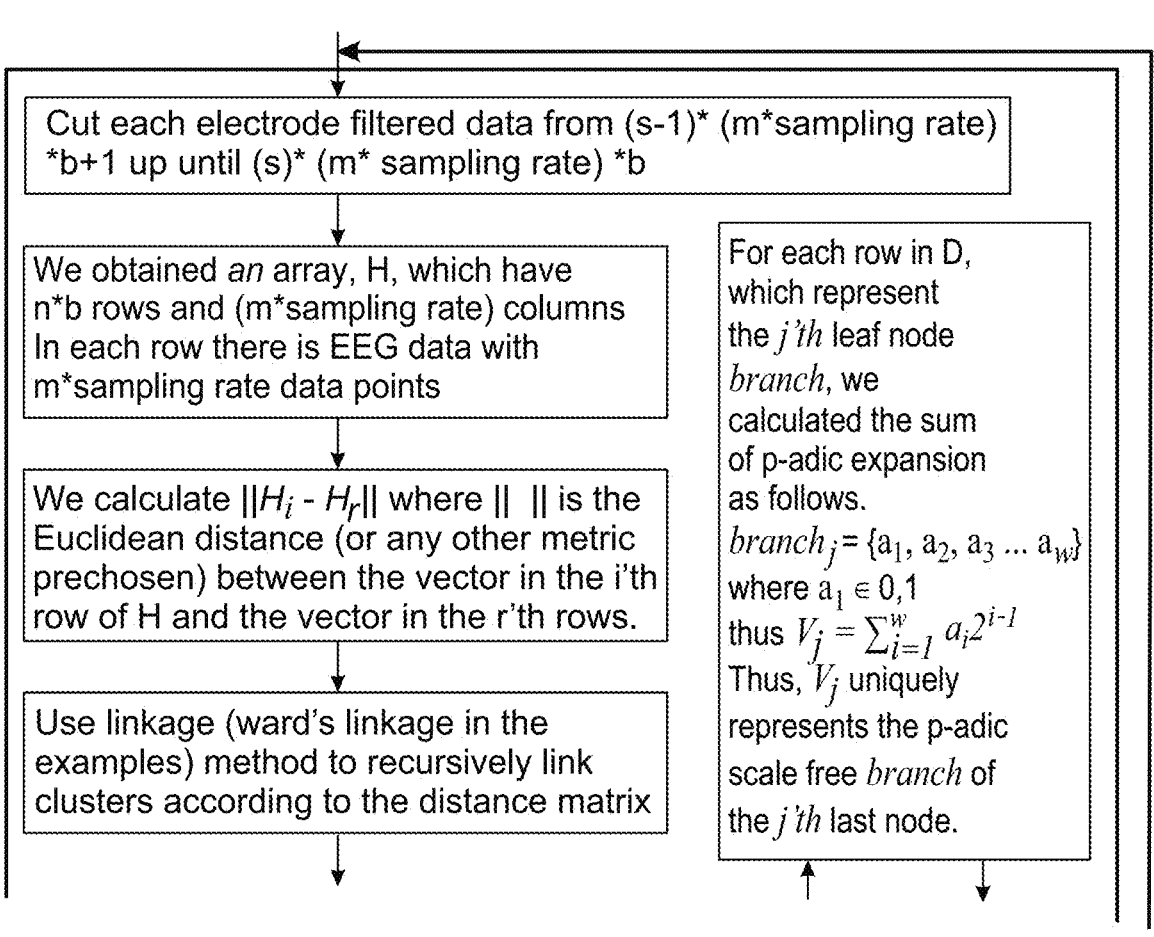

Cut each electrode filtered data from (s-1)* (m*sampling rate) *b+1 up until (s)* (m* sampling rate) *b We obtained *an* array, H, which have n*b rows and (m*sampling rate) columns In each row there is EEG data with m*sampling rate data points We calculate $\|H_i - H_r\|$ where $\| \; \|$ is the Euclidean distance (or any other metric prechosen) between the vector in the i'th row of H and the vector in the r'th rows.

Use linkage (ward's linkage in the examples) method to recursively link clusters according to the distance matrix For each row in D, which represent the *j'th* leaf node *branch*, we calculated the sum of p-adic expansion as follows.
$branch_j = \{a_1, a_2, a_3 \dots a_w\}$
where $a_1 \in 0,1$
thus $V_j = \sum_{i=1}^{w} a_i 2^{i-1}$
Thus, $V_j$ uniquely represents the p-adic scale free *branch* of the *j'th* last node.

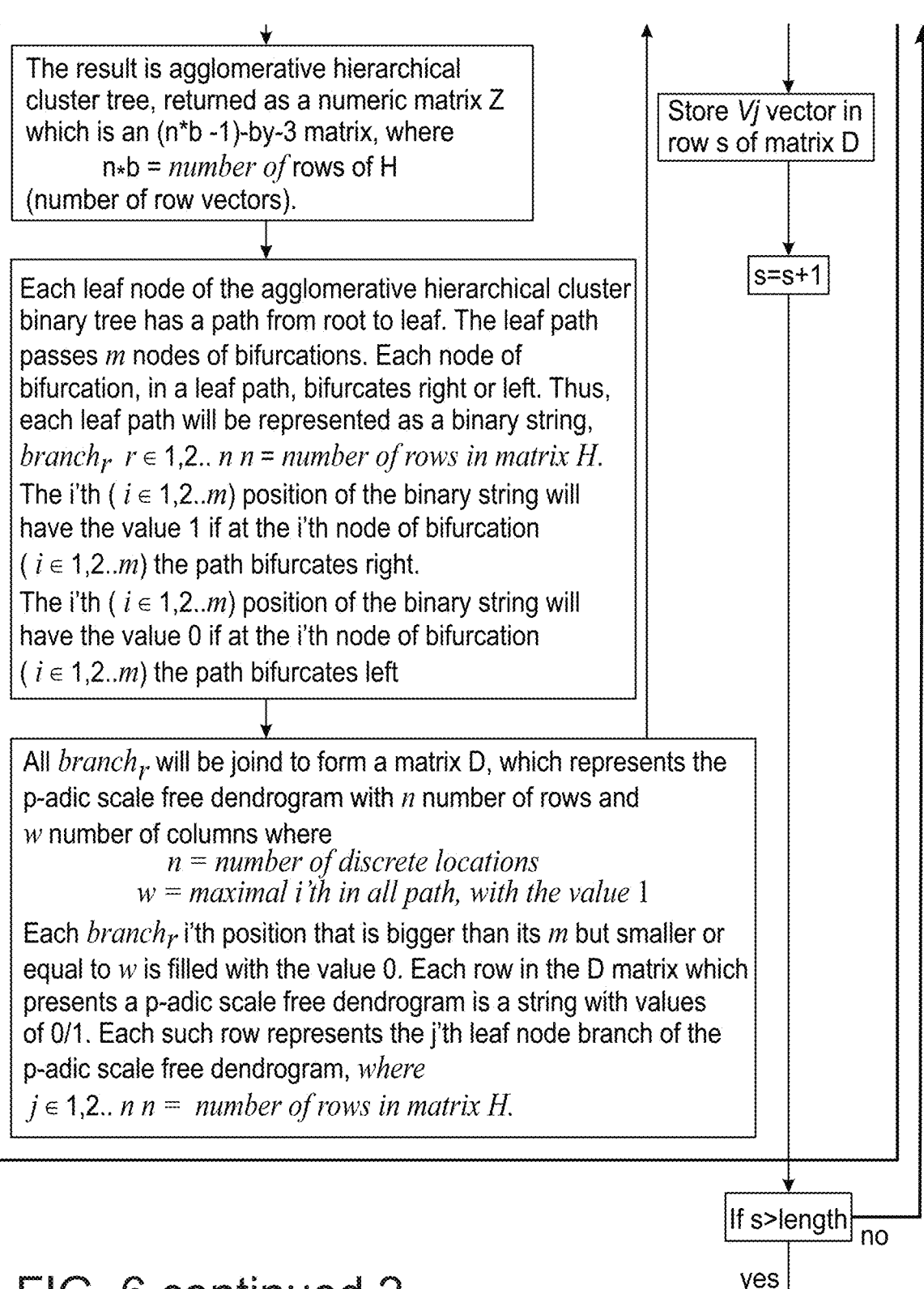

The result is agglomerative hierarchical cluster tree, returned as a numeric matrix Z which is an (n*b -1)-by-3 matrix, where
$$n*b = number\ of\ \text{rows of H}$$
(number of row vectors).

Each leaf node of the agglomerative hierarchical cluster binary tree has a path from root to leaf. The leaf path passes $m$ nodes of bifurcations. Each node of bifurcation, in a leaf path, bifurcates right or left. Thus, each leaf path will be represented as a binary string, $branch_r$ $r \in 1,2.. n$ $n = number\ of\ rows\ in\ matrix\ H$. The i'th ( $i \in 1,2..m$) position of the binary string will have the value 1 if at the i'th node of bifurcation ( $i \in 1,2..m$) the path bifurcates right.
The i'th ( $i \in 1,2..m$) position of the binary string will have the value 0 if at the i'th node of bifurcation ( $i \in 1,2..m$) the path bifurcates left All $branch_r$ will be joind to form a matrix D, which represents the p-adic scale free dendrogram with $n$ number of rows and $w$ number of columns where
$$n = number\ of\ discrete\ locations$$
$$w = maximal\ i'th\ in\ all\ path,\ with\ the\ value\ 1$$
Each $branch_r$ i'th position that is bigger than its $m$ but smaller or equal to $w$ is filled with the value 0. Each row in the D matrix which presents a p-adic scale free dendrogram is a string with values of 0/1. Each such row represents the j'th leaf node branch of the p-adic scale free dendrogram, $where$
$$j \in 1,2.. n \quad n = number\ of\ rows\ in\ matrix\ H.$$

Store $Vj$ vector in row s of matrix D s=s+1

If s>length no yes

FIG. 6 continued 2

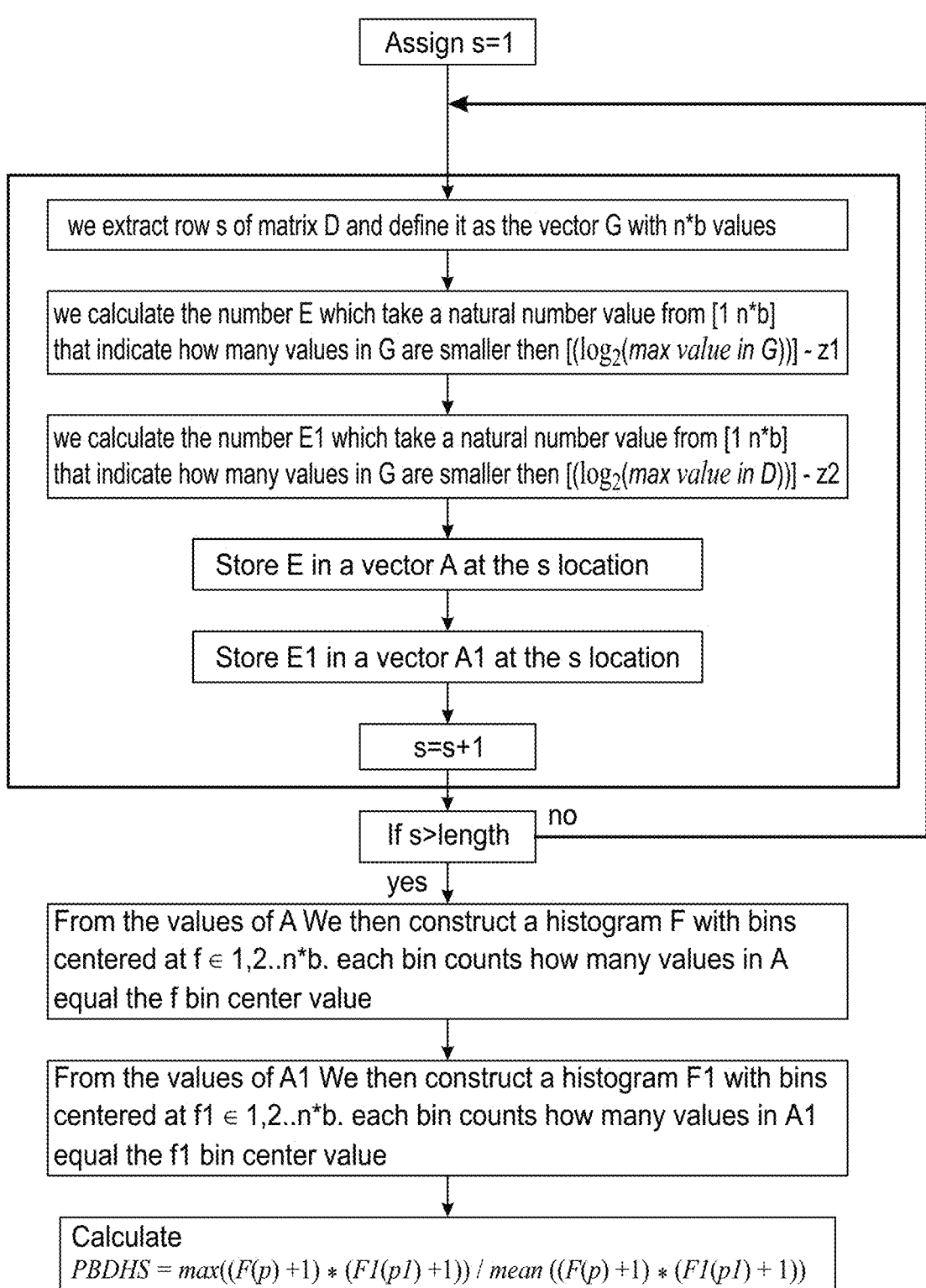

Assign s=1 we extract row s of matrix D and define it as the vector G with n*b values we calculate the number E which take a natural number value from [1 n*b] that indicate how many values in G are smaller then [(log$_2$(*max value in G*))] - z1 we calculate the number E1 which take a natural number value from [1 n*b] that indicate how many values in G are smaller then [(log$_2$(*max value in D*))] - z2

Store E in a vector A at the s location

Store E1 in a vector A1 at the s location s=s+1

If s>length    no yes

From the values of A We then construct a histogram F with bins centered at f ∈ 1,2..n*b. each bin counts how many values in A equal the f bin center value From the values of A1 We then construct a histogram F1 with bins centered at f1 ∈ 1,2..n*b. each bin counts how many values in A1 equal the f1 bin center value Calculate
$PBDHS = max((F(p) +1) * (F1(p1) +1)) / mean ((F(p) +1) * (F1(p1) + 1))$

FIG. 6 continued 3

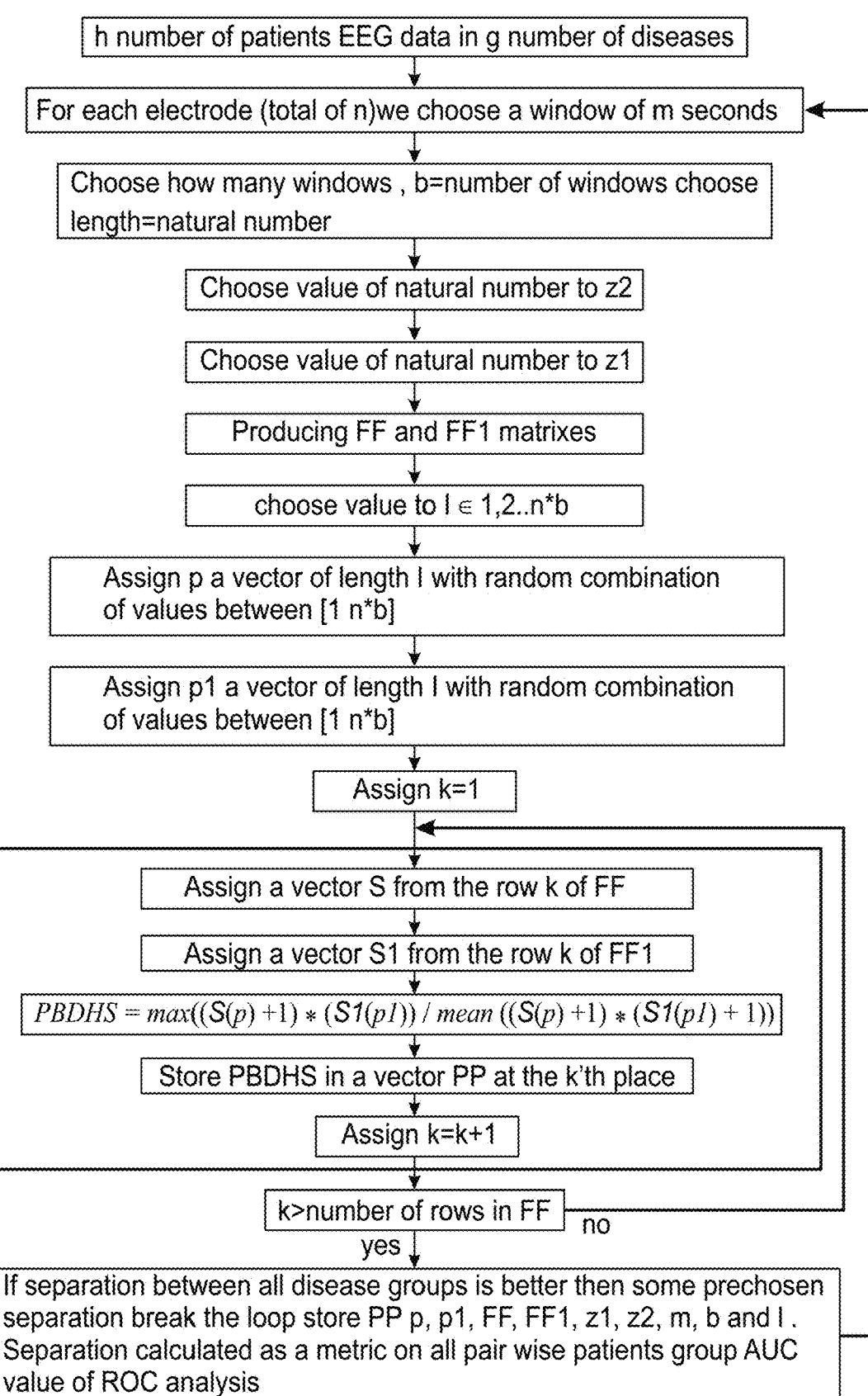

h number of patients EEG data in g number of diseases

For each electrode (total of n)we choose a window of m seconds

Choose how many windows , b=number of windows choose length=natural number

Choose value of natural number to z2

Choose value of natural number to z1

Producing FF and FF1 matrixes choose value to $l \in 1,2..n*b$

Assign p a vector of length l with random combination of values between [1 n*b]

Assign p1 a vector of length l with random combination of values between [1 n*b]

Assign k=1

Assign a vector S from the row k of FF

Assign a vector S1 from the row k of FF1

$PBDHS = max((S(p) +1) * (S1(p1)) / mean ((S(p) +1) * (S1(p1) + 1))$

Store PBDHS in a vector PP at the k'th place

Assign k=k+1 k>number of rows in FF          no yes

If separation between all disease groups is better then some prechosen separation break the loop store PP p, p1, FF, FF1, z1, z2, m, b and l . Separation calculated as a metric on all pair wise patients group AUC value of ROC analysis

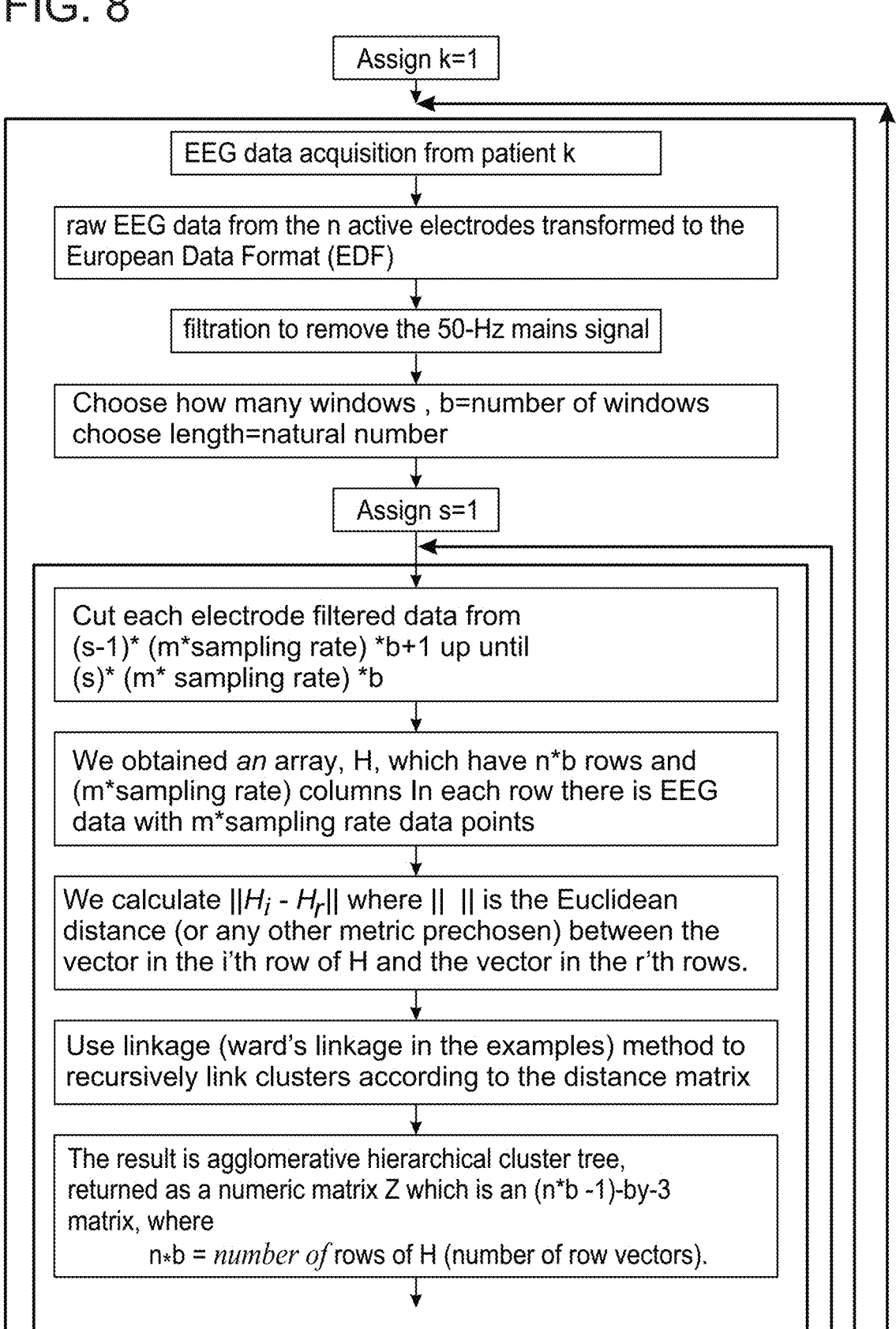

Assign k=1

EEG data acquisition from patient k raw EEG data from the n active electrodes transformed to the European Data Format (EDF)

filtration to remove the 50-Hz mains signal

Choose how many windows , b=number of windows choose length=natural number

Assign s=1

Cut each electrode filtered data from $(s-1)*(m*sampling\ rate)*b+1$ up until $(s)*(m*sampling\ rate)*b$ We obtained *an* array, H, which have n*b rows and (m*sampling rate) columns In each row there is EEG data with m*sampling rate data points We calculate $\|H_i - H_r\|$ where $\|\ \|$ is the Euclidean distance (or any other metric prechosen) between the vector in the i'th row of H and the vector in the r'th rows.

Use linkage (ward's linkage in the examples) method to recursively link clusters according to the distance matrix The result is agglomerative hierarchical cluster tree, returned as a numeric matrix Z which is an (n*b -1)-by-3 matrix, where
        n*b = *number of* rows of H (number of row vectors).

FIG. 8 continued

Each leaf node of the agglomerative hierarchical cluster binary tree has a path from root to leaf. The leaf path passes $m$ nodes of bifurcations. Each node of bifurcation, in a leaf path, bifurcates right or left. Thus, each leaf path will be represented as a binary string, $branch_r$ $r \in 1,2.. n$ $n = number\ of\ rows\ in\ matrix\ H$. The i'th ( $i \in 1,2..m$) position of the binary string will have the value 1 if at the i'th node of bifurcation ( $i \in 1,2..m$) the path bifurcates right. The i'th ( $i \in 1,2..m$) position of the binary string will have the value 0 if at the i'th node of bifurcation ( $i \in 1,2..m$) the path bifurcates left All $branch_r$ will be joind to form a matrix D, which represents the p-adic scale free dendrogram with $n$ number of rows and $w$ number of columns where
$$n = number\ of\ discrete\ locations$$
$$w = maximal\ i'th\ in\ all\ path,\ with\ the\ value\ 1$$
Each $branch_r$ i'th position that is bigger than its $m$ but smaller or equal to $w$ is filled with the value 0. Each row in the D matrix which presents a p-adic scale free dendrogram is a string with values of 0/1. Each such row represents the j'th leaf node branch of the p-adic scale free dendrogram, $where$
$$j \in 1,2.. n\ n = number\ of\ rows\ in\ matrix\ H.$$

For each row in D, which represent the $j'th$ leaf node $branch$, we calculated the sum of p-adic expansion as follows.
$branch_j = \{a_1, a_2, a_3 ... a_w\}$ where $a_1 \in 0,1$ thus $V_j = \sum_{i=1}^{w} a_i 2^{i-1}$
Thus, $V_j$ uniquely represents the p-adic scale free $branch$ of the $j'th$ last node.

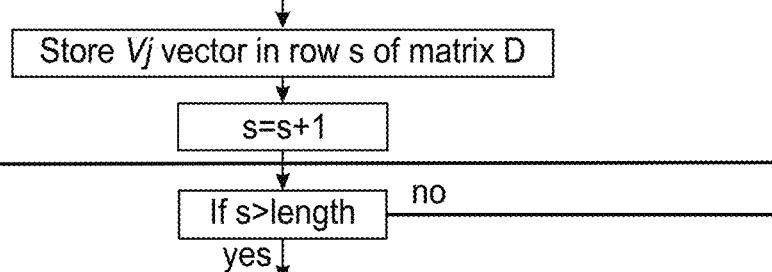

Store $Vj$ vector in row s of matrix D $s=s+1$

If s>length —— no yes

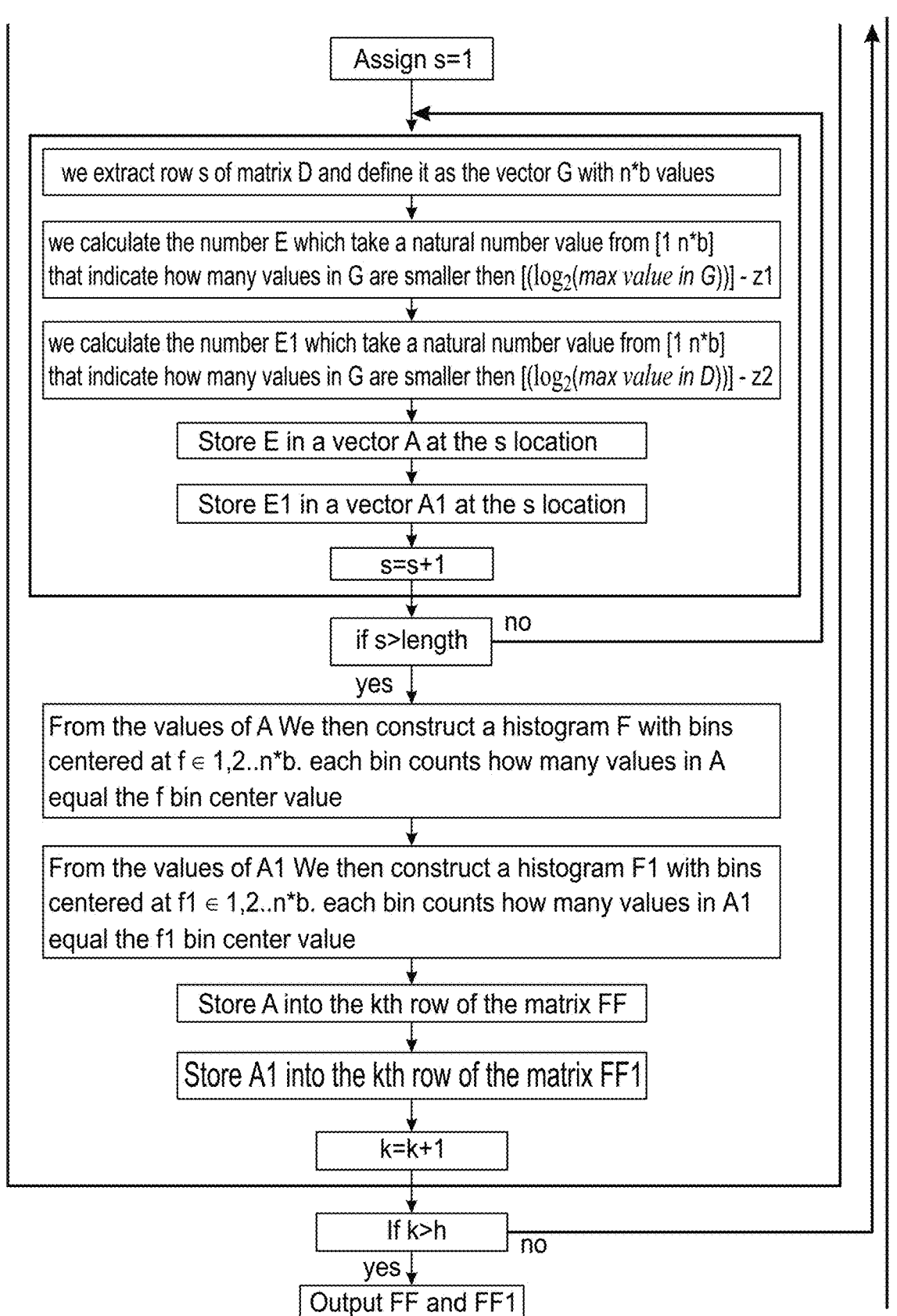

Assign s=1 we extract row s of matrix D and define it as the vector G with n*b values we calculate the number E which take a natural number value from [1 n*b] that indicate how many values in G are smaller then $[(\log_2(max\ value\ in\ G))]$ - z1 we calculate the number E1 which take a natural number value from [1 n*b] that indicate how many values in G are smaller then $[(\log_2(max\ value\ in\ D))]$ - z2

Store E in a vector A at the s location

Store E1 in a vector A1 at the s location s=s+1 if s>length          no yes

From the values of A We then construct a histogram F with bins centered at f $\in$ 1,2..n*b. each bin counts how many values in A equal the f bin center value From the values of A1 We then construct a histogram F1 with bins centered at f1 $\in$ 1,2..n*b. each bin counts how many values in A1 equal the f1 bin center value Store A into the kth row of the matrix FF Store A1 into the kth row of the matrix FF1 k=k+1

If k>h          no yes

Output FF and FF1

FIG. 8 continued 2

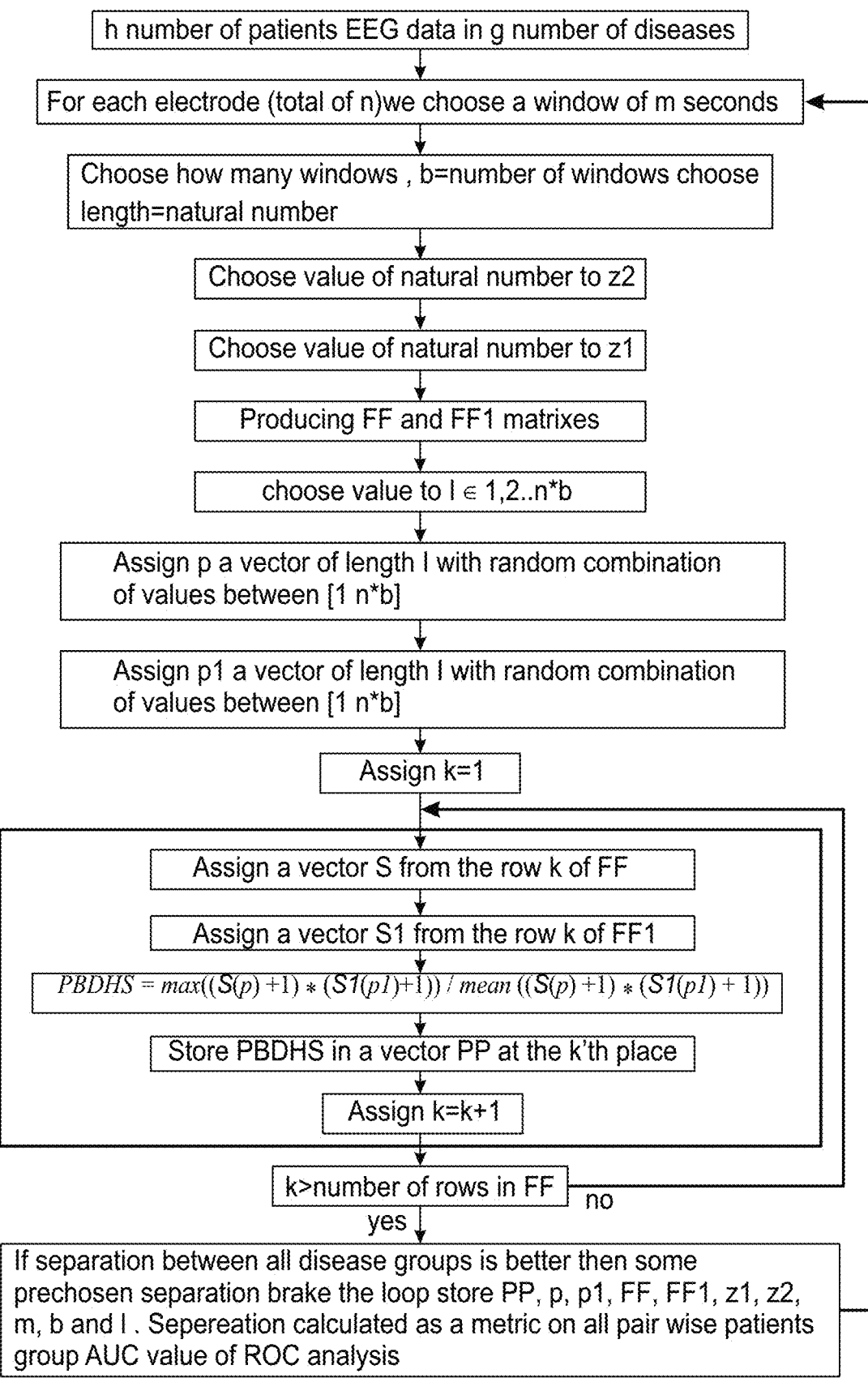

h number of patients EEG data in g number of diseases

For each electrode (total of n)we choose a window of m seconds

Choose how many windows , b=number of windows choose length=natural number

Choose value of natural number to z2

Choose value of natural number to z1

Producing FF and FF1 matrixes choose value to $l \in 1,2..n*b$

Assign p a vector of length l with random combination of values between [1 n*b]

Assign p1 a vector of length l with random combination of values between [1 n*b]

Assign k=1

Assign a vector S from the row k of FF

Assign a vector S1 from the row k of FF1

$PBDHS = max((S(p) +1) * (S1(p1)+1)) / mean ((S(p) +1) * (S1(p1) + 1))$

Store PBDHS in a vector PP at the k'th place

Assign k=k+1 k>number of rows in FF          no yes

If separation between all disease groups is better then some prechosen separation brake the loop store PP, p, p1, FF, FF1, z1, z2, m, b and l . Sepereation calculated as a metric on all pair wise patients group AUC value of ROC analysis

FIG. 9

PERSONAL UNIVERSAL DENDROGRAMIC HOLOGRAPHIC SIGNATURE FROM EEG DATA ANALYSIS FOR DIAGNOSIS OF NEURO-PSYCHIATRIC DISEASES

RELATED APPLICATION APPLICATIONS

This application is a National Phase of PCT Patent Application No. PCT/IL2023/050252 having International filing date of Mar. 10, 2023, which claims the benefit of priority under 35 USC § 119 (e) of U.S. Provisional Patent Application No. 63/319,416 filed on Mar. 14, 2022. The contents of the above applications are all incorporated by reference as if fully set forth herein in their entirety.

FIELD AND BACKGROUND OF THE INVENTION

The present invention, in some embodiments thereof, relates to diagnosing neuro-psychiatric diseases and, more specifically, but not exclusively, to systems and methods for diagnosing neuro-psychiatric diseases using EEG data.

Most psychiatric disorders are diagnosed clinically based on the patient's history with the combination of physician assessment of the mental state, level of consciousness, cognitive evaluation, and mood evaluation. These assessments are carried by a series of interviews and can be accompanied by neurologic examinations. (Livingston et al., 2017; Malhi & Mann, 2018; Owen, Sawa, & Mortensen, 2016, incorporated herein by reference in their entirety). These tools enable the diagnostic upon which clinical treatment decisions can be made, but they are largely subjective and prone to inaccuracies. Consequently, diagnosis and treatment are often delayed to an advanced stage of the disease. This in turn causes the therapeutic interventions to be less efficient with the increased risk for the patient not to fully recover. (Collins, Insel, Chockalingam, Daar, & Maddox, 2013; Keynejad, Dua, Barbui, & Thornicroft, 2018, incorporated herein by reference in their entirety)

SUMMARY OF THE INVENTION

According to a first aspect, a computer implemented method of diagnosing a medical state associated with a neuro-psychiatric disorder in a subject, comprises: receiving a plurality of EEG datasets from a plurality of EEG electrodes monitoring a head of the subject, computing a plurality of events for the plurality of EEG datasets, clustering the plurality of events into a plurality of clusters, computing a p-adic representation of the plurality of clusters, extracting a p-adic topology from the p-adic representation of the plurality of clusters, computing a personal universal dendrogramic holographic signature (PUDHS) of the p-acid topology relative to a personalized threshold that separates between a relative large distance between events and a relatively small distance between events, the PUDHS denoting number of events below the personalized threshold, and diagnosing the medical state associated with the neuro-psychiatric disorder according to the PUDHS relative to a medical threshold that separates between presence of the medical state and non-presence of the medical state.

According to a second aspect, a computer implemented method of diagnosing a medical state associated with a neuro-psychiatric disorder in a subject, comprises: receiving a plurality of EEG datasets from a plurality of EEG electrodes monitoring a head of the subject, dividing the plurality of EEG datasets into a plurality of time intervals, grouping the plurality of EEG datasets divided into time intervals into a plurality of groups, each group including divided EEG datasets obtained during a common time interval, for each group: computing a plurality of events, clustering the plurality of events into a plurality of clusters, computing a p-adic representation of the plurality of clusters, extracting a p-adic topology from the p-adic representation of the plurality of clusters, computing a time series of a plurality of p-adic topologies, each respective p-adic topology computed for each respective group, computing a personal block DH signature (PBDHS) of the time series of the plurality of p-adic topologies relative to a first personalized threshold and a second personalized threshold, wherein the first personalized threshold is computed for each respective p-adic topology of the time series, the first personalized threshold separates between a relative large distance between events of the respective p-adic topology and a relatively small distance between events of the p-adic topology, wherein the second personalized threshold is computed for all p-adic topologies of the time series, the second personalized threshold separates between a relative large distance between events of the p-adic topologies of the time series and a relatively small distance between events of the p-adic topologies of the time series, and diagnosing the medical state associated with the neuro-psychiatric disorder according to the PBDHS relative to a medical threshold that separates between presence of the medical state and non-presence of the medical state.

According to a third aspect, a system for diagnosing a medical state associated with a neuro-psychiatric disorder in a subject, comprises: at least one processor executing a code for: receiving a plurality of EEG datasets from a plurality of EEG electrodes monitoring a head of the subject, computing a plurality of events for the plurality of EEG datasets, clustering the plurality of events into a plurality of clusters, computing a p-adic representation of the plurality of clusters, extracting a p-adic topology from the p-adic representation of the plurality of clusters, computing a personal universal DH signature (PUDHS) of the p-acid topology relative to a personalized threshold that separates between a relative large distance between events and a relatively small distance between events, the PUDHS denoting number of events below the personalized threshold, and diagnosing the medical state associated with the neuro-psychiatric disorder according to the PUDHS relative to a medical threshold that separates between presence of the medical state and non-presence of the medical state.

According to a fourth aspect, a system for diagnosing a medical state associated with a neuro-psychiatric disorder in a subject, comprises: at least one processor executing a code for: receiving a plurality of EEG datasets from a plurality of EEG electrodes monitoring a head of the subject, dividing the plurality of EEG datasets into a plurality of time intervals, grouping the plurality of EEG datasets divided into time intervals into a plurality of groups, each group including divided EEG datasets obtained during a common time interval, for each group: computing a plurality of events, clustering the plurality of events into a plurality of clusters, computing a p-adic representation of the plurality of clusters, extracting a p-adic topology from the p-adic representation of the plurality of clusters, computing a time series of a plurality of p-adic topologies, each respective p-adic topology computed for each respective group, computing a personal block DH signature (PBDHS) of the time series of the plurality of p-adic topologies relative to a first personalized threshold and a second personalized threshold, wherein the first personalized threshold is computed for each respective p-adic topology of the time series, the first personalized threshold separates between a relative large distance between events of the respective p-adic topology and a relatively small distance between events of the p-adic topology, wherein the second personalized threshold is computed for all p-adic topologies of the time series, the second personalized threshold separates between a relative large distance between events of the p-adic topologies of the time series and a relatively small distance between events of the p-adic topologies of the time series, and diagnosing the medical state associated with the neuro-psychiatric disorder according to the PBDHS relative to a medical threshold that separates between presence of the medical state and non-presence of the medical state.

In a further implementation form of the first, and third aspects, the p-adic representation comprises a dendrogram, wherein each branch of the dendrogram represents a respective event.

In a further implementation form of the first, and third aspects, the PUDHS denotes a number of branches of the dendrogram smaller than the personalized threshold.

In a further implementation form of the first, and third aspects, the dendrogram comprises a homogenous tree with a same number of edges for each vertex, wherein each vertex includes one incoming edge and two outgoing edges.

In a further implementation form of the first, and third aspects, each branch of the dendrogram is labeled by a binary number denoting a natural number encoding each respective branch, wherein a set of all branches is a 2D structure denoting the p-acid topology of the dendrogram, wherein the p-adic representation of each respective branch encodes relations of the respective branch to all other branches, wherein a distance between natural numbers is denoted by a common root-branch, wherein a longer common root indicates a shorter distance.

In a further implementation form of the first, and third aspects, the p-adic representation indicates relative and non-absolute relationships between the events.

In a further implementation form of the first, and third aspects, further comprising computing a plurality of distances, each respective distance computed for a respective pair of EEG datasets, wherein clustering comprises computing a hierarchical relationship between the plurality of distances, wherein the p-acid representation is computed according to the hierarchical relationship.

In a further implementation form of the first, and third aspects, the personalized threshold is computed as being lower than a maximal p-adic ball of the p-adic topology by a parameter, wherein the parameter is fixed at a same value for other subjects.

In a further implementation form of the first, and third aspects, the personalized threshold is computed individually for each subject, and varies between subjects according to the respective p-adic topology of the respective subject.

In a further implementation form of the first, and third aspects, each respective event is computed as at least one of: a vector representation of a respective EEG dataset, and a time interval of a selected length of the respective EEG dataset.

In a further implementation form of the first, and third aspects, the threshold that separates between presence of the medical state and non-presence of the medical state is set by: computing a plurality of PUDHS values, each PUDHS value for one of a plurality of subjects associated with an indication of the medical state or an indication of non-presence of the medical state, using respective EEG datasets, and setting the threshold to separate between PUDHS values of subjects associated with the indication of the medical state, and PUDHS values of subjects associated with the indication of non-presence of the medical state.

In a further implementation form of the first, and third aspects, p-adic comprises 2-adic.

In a further implementation form of the first, and third aspects, further comprising treating the patient using a treatment effective for the medical state, selected from a group consisting of: psychotherapy, anti-depressant medication, anti-psychotic medication, electroconvulsive therapy (ECT), and transcranial magnetic stimulation (TMS).

In a further implementation form of the first, and third aspects, the medical state is selected from the group consisting of: depression, schizophrenia, Alzheimer's disease (AD), and mild cognitive impairment (MCI), and the non-presence of the medical state is selected from the group consisting of: no neuro-psychiatric disorder, and another neuro-psychiatric disorder that is different from the medical state.

In a further implementation form of the first, and third aspects, the medical state is selected from the group consisting of: stable AD, stable MCI and the non-presence of the medical state is selected from the group consisting of: deteriorating AD, and deteriorating MCI.

In a further implementation form of the first, and third aspects, the medical state comprises a prediction of likelihood of developing the neuro-psychiatric disorder in the future, and the non-presence of the medical state comprises a prediction of likelihood of not developing the neuro-psychiatric disorder in the future.

In a further implementation form of the first, and third aspects, the medical state comprises a prediction of likelihood of positively clinically significantly responding to a certain treatment for the neuro-psychiatric disorder, and the non-presence of the medical state comprises a prediction of likelihood of no clinically significant response to the certain treatment for the neuro-psychiatric disorder.

In a further implementation form of the first, and third aspects, further comprising: computing a first PUDHS value for the subject prior to administration of a certain treatment for the neuro-psychiatric disorder, administering the certain treatment to the subject, computing a second PUDHS value for the subject after the administration of the certain treatment for the neuro-psychiatric disorder, and determining a clinically significant response to the certain treatment when the second PUDHS value is statistically significantly different from the first PUDHS value.

In a further implementation form of the second, and fourth aspects, the first personalized threshold for a respective p-adic topology is computed as being lower than a maximal p-adic ball of the respective p-adic topology by a first parameter fixed at a same value for the other p-adic topologies of other subjects.

In a further implementation form of the second, and fourth aspects, the second personalized threshold for a respective p-adic topology is computed as being lower than a maximal p-adic ball of the p-adic topologies of the time series by a second parameter, wherein the second parameter is fixed at a same value for the other p-adic topologies of other subjects.

In a further implementation form of the second, and fourth aspects, the p-adic representation comprises a dendrogram, wherein each branch of the dendrogram represents a respective event.

In a further implementation form of the second, and fourth aspects, the dendrogram comprises a homogenous tree with a same number of edges for each vertex, wherein each vertex includes one incoming edge and two outgoing edges.

In a further implementation form of the second, and fourth aspects, each branch of the dendrogram is labeled by a binary number denoting a natural number encoding each respective branch, wherein a set of all branches is a 2D structure denoting the p-acid topology of the dendrogram, wherein the p-adic representation of each respective branch encodes relations of the respective branch to all other branches, wherein a distance between natural numbers is denoted by a common root-branch, wherein a longer common root indicates a shorter distance.

In a further implementation form of the second, and fourth aspects, the p-adic representation indicates relative and non-absolute relationships between the events.

In a further implementation form of the second, and fourth aspects, further comprising computing a plurality of distances, each respective distance computed for a respective pair of EEG datasets, wherein clustering comprises computing a hierarchical relationship between the plurality of distances, wherein the p-acid representation is computed according to the hierarchical relationship.

In a further implementation form of the second, and fourth aspects, the first personalized threshold and the second personalized threshold is computed as being lower than a maximal p-adic ball of the p-adic topology by a parameter, wherein the parameter is fixed at a same value for other subjects.

In a further implementation form of the second, and fourth aspects, the first personalized threshold and the second personalized threshold are computed individually for each subject, and vary between subjects according to the respective p-adic topology of the respective subject.

In a further implementation form of the second, and fourth aspects, each respective event is computed as at least one of: a vector representation of a respective EEG dataset, and a time interval of a selected length of the respective EEG dataset.

In a further implementation form of the second, and fourth aspects, the medical threshold that separates between presence of the medical state and non-presence of the medical state is set by: computing a plurality of PBDHS values, each PBDHS value for one of a plurality of subjects associated with an indication of the medical state or an indication of non-presence of the medical state, using respective EEG datasets, and setting the threshold to separate between PBDHS values of subjects associated with the indication of the medical state, and PBDHS values of subjects associated with the indication of non-presence of the medical state.

In a further implementation form of the second, and fourth aspects, p-adic comprises 2-adic.

In a further implementation form of the second, and fourth aspects, further comprising treating the patient using a treatment effective for the medical state, selected from a group consisting of: psychotherapy, anti-depressant medication, anti-psychotic medication, electroconvulsive therapy (ECT), and transcranial magnetic stimulation (TMS).

In a further implementation form of the second, and fourth aspects, the medical state is selected from the group consisting of: depression, schizophrenia, Alzheimer's disease (AD), and mild cognitive impairment (MCI), and the non-presence of the medical state is selected from the group consisting of: no neuro-psychiatric disorder, and another neuro-psychiatric disorder that is different from the medical state.

In a further implementation form of the second, and fourth aspects, the medical state is selected from the group consisting of: stable AD, stable MCI and the non-presence of the medical state is selected from the group consisting of: deteriorating AD, and deteriorating MCI.

In a further implementation form of the second, and fourth aspects, the medical state comprises a prediction of likelihood of developing the neuro-psychiatric disorder in the future, and the non-presence of the medical state comprises a prediction of likelihood of not developing the neuro-psychiatric disorder in the future.

In a further implementation form of the second, and fourth aspects, the medical state comprises a prediction of likelihood of positively clinically significantly responding to a certain treatment for the neuro-psychiatric disorder, and the non-presence of the medical state comprises a prediction of likelihood of no clinically significant response to the certain treatment for the neuro-psychiatric disorder.

In a further implementation form of the second, and fourth aspects, further comprising: computing a first PBDHS value for the subject prior to administration of a certain treatment for the neuro-psychiatric disorder, administering the certain treatment to the subject, computing a second PBDHS value for the subject after the administration of the certain treatment for the neuro-psychiatric disorder, and determining a clinically significant response to the certain treatment when the second PBDHS value is statistically significantly different from the first PBDHS value.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7 is a flowchart of a method for maximizing discrimination levels between groups by performing the PBDHS calculation with different z1 and z2 combinations, in accordance with some embodiments of the present invention;

FIG. 8 is a flowchart of a method for computing FF and FF1, in accordance with some embodiments of the present invention;

FIG. 9 is a flowchart of an exemplary method of selecting PP, p, p1, FF, FF1, z1, z2, m, and b values using machine learning approaches for providing separation of patient groups for computation of PBDHS values, in accordance with some embodiments of the present invention;

DESCRIPTION OF SPECIFIC EMBODIMENTS OF THE INVENTION

Figure 1A:
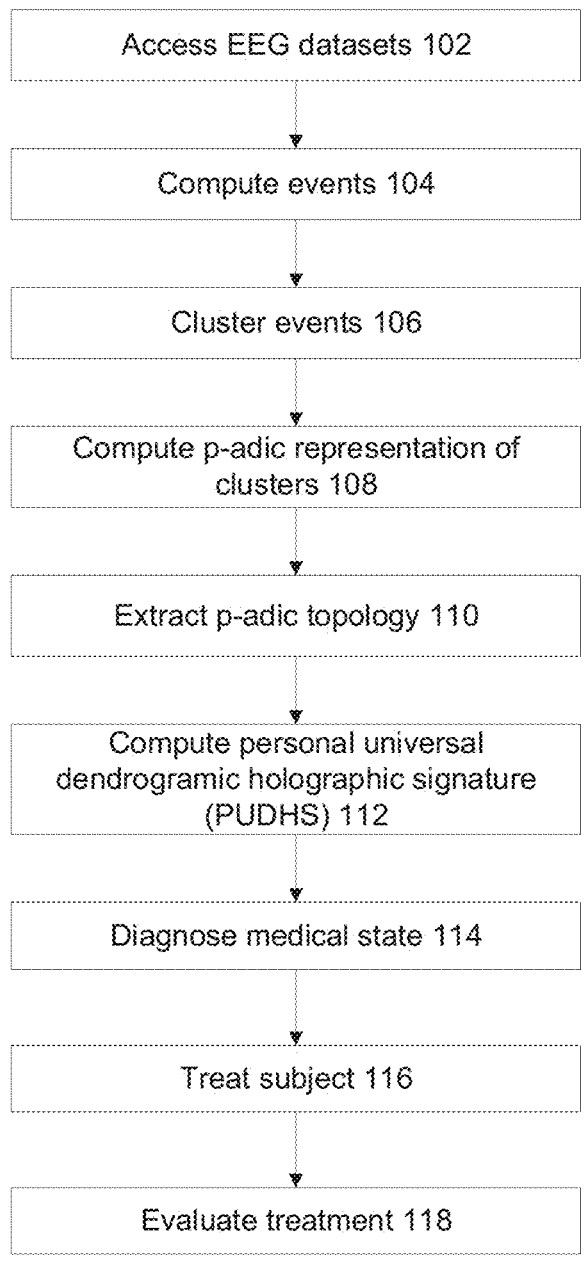
FIG. 1A is a flowchart of a method of computing a personal universal dendrogramic holographic signature (PUDHS) for a subject, in accordance with some embodiments of the present invention.

The present invention, in some embodiments thereof, relates to diagnosing neuro-psychiatric diseases and, more specifically, but not exclusively, to systems and methods for diagnosing neuro-psychiatric diseases using EEG data.

An aspect of some embodiments of the present invention relate to systems, methods, computing devices, and/or code instructions (stored in a memory and executable by one or more processors) for computing a personal universal dendrogramic holographic signature (PUDHS) of a subject. A processor accesses EEG datasets obtained from EEG electrodes monitoring a head of the subject. The processor computes events for the EEG datasets. The events are clustered into multiple clusters. A p-adic representation of the clusters is computed. A p-adic topology is extracted from the p-adic representation of the clusters. The processor computes the PUDHS of the p-acid topology relative to a personalized threshold that separates between a relative large distance between events and a relatively small distance between events. The PUDHS denotes the number of events below the personalized threshold. The PUDHS may be used for diagnosing a medical state of the subject associated with a neuro-psychiatric disorder, according to the PUDHS relative to a medical threshold that separates between presence of the medical state and non-presence of the medical state.

An aspect of some embodiments of the present invention relate to systems, methods, computing devices, and/or code instructions (stored in a memory and executable by one or more processors) for computing a personal block DH signature (PBDHS) of a subject. A processor accesses EEG datasets obtained from EEG electrodes monitoring a head of the subject. The EEG datasets are divided into time intervals. The EEG datasets divided into time intervals are grouped into groups. Each group includes divided EEG datasets obtained during a common time interval. For each group the processor: computes events, clusters the events into clusters, computes a p-adic representation of the clusters, and extracts a p-adic topology from the p-adic representation of the clusters. The processor computes a time series of p-adic topologies, where each respective p-adic topology is computed for each respective group. The processor computes a PBDHS of the time series of the plurality of p-adic topologies relative to a first personalized threshold and a second personalized threshold. The first personalized threshold is computed for each respective p-adic topology of the time series. The first personalized threshold separates between a relative large distance between events of the respective p-adic topology and a relatively small distance between events of the p-adic topology. The second personalized threshold is computed for all p-adic topologies of the time series. The second personalized threshold separates between a relative large distance between events of the p-adic topologies of the time series and a relatively small distance between events of the p-adic topologies of the time series. The PBDHS may be used for diagnosing the medical state associated with the neuro-psychiatric disorder, according to the PBDHS relative to a medical threshold that separates between presence of the medical state and non-presence of the medical state.

Examples of medical states associated with the neuro-psychiatric disorder in a subject which may be diagnosed using the PUDHS and/or PBDHS computed from EEG datasets obtained from EEG electrodes monitoring a head of a subject, include: depression, schizophrenia, anxiety disorder, Alzheimer's disease, mild cognitive impairment, epileptic seizures, differentiating between no neuro-psychiatric condition and the presence of the neuro-psychiatric condition, differentiating between two different neuro-psychiatric conditions, predicting likelihood of developing the neuro-psychiatric disorder in the future (e.g., when no clinically significant symptoms current exist to diagnose the neuro-psychiatric disorder), predicting likelihood of a clinically significant response to a certain treatment administered for treating the neuro-psychiatric disorder, and/or for evaluating response to a certain treatment applied to the patient for treating the neuro-psychiatric disorder.

The neuro-psychiatric disorders described herein are disorders of the brain, including neurological as well psychiatric disorders. Neuro-psychiatric diseases involve the brain, spinal cord and/or the peripheral nervous system and are primarily even though artificially categorized into neurological and psychiatric disorders. The neurological disorders include, for example, one or more of: cerebrovascular diseases (e.g. stroke), central nervous system trauma, seizure disorders and epilepsy, progressive neurodegenerative diseases (e.g. Alzheimer's dementia, Parkinson's disease, Motor Neuron Disease, Huntington's disease), neuroinflammatory diseases (e.g. Multiple sclerosis, systemic lupus erythematosus), central nervous system tumors, infectious diseases of the nervous system, developmental disorders of the CNS including genetic disorders (Down syndrome, Fragile-x, Autism Spectrum disorder), Acquired metabolic disorders of the CNS, diseases of the CNS caused by malnutrition, toxins or drug abuse. The psychiatric disorders, may be categorized according to the ICD-10, for example, including organic, including symptomatic, mental disorders, organic amnesic syndrome, personality and behavioral disorder, mental and behavioral disorders due to psychoactive substance use, schizophrenia, schizotypal and delusional disorders, schizoaffective disorders, mood (affective) disorders (e.g. mania, bipolar and depression), neurotic, stress-related and somatoform disorders (e.g. anxiety disorders), somatoform disorders, eating disorders, personality disorders, intellectual disability.

As used herein, the terms neuro-psychiatric disorder and brain disorder are interchangeable.

At least some implementations of the systems, methods, apparatus, and/or code instructions described herein address the technical problem and/or medical problem of an objective, repeatable, and/or automated process for diagnosing and/or computing a biomarker indicative of likelihood of a brain disorder in a subject, and/or for determining effectiveness of a treatment for the brain disorder. At least some implementations of the systems, methods, apparatus, and/or code instructions described herein improve the technical field and/or the medical field of diagnosing and/or computing a biomarker indicative of likelihood of a brain disorder in a subject, and/or for determining effectiveness of a treatment for the brain disorder.

Electroencephalography (EEG) is widely used inexpensive and well established in healthcare systems around the world (Cervenka & Kaplan, 2016; Smith, 2005, incorporated herein by reference in their entirety). it is an inexpensive diagnostic tool used primarily for the diagnosis of Epilepsy. various EEG signature activity such as resting-state power, spectral and functional connectivity analyses as well as microstate analysis have been proven capable to identify patients with a pre-diagnosis of schizophrenia (Baradits et al., 2019; Endres et al., 2016; Maran, Grent-'t-Jong, & Uhlhaas, 2016; Oh, Vicnesh, Ciaccio, Yuvaraj, & Acharya, 2019, incorporated herein by reference in their entirety), and depression (Arns & Gordon, 2014; Newson & Thiagarajan, 2018; Olbrich & Arns, 2013; Wade & Iosifescu, 2016; C.-T. Wu et al., 2018, incorporated herein by reference in their entirety) with variable success and lack of use in clinical practice.

The approach described herein to the medical diagnostic of neuro-psychiatric diseases and more generally analysis of the mental states is based on an adaptation of Dendrogramic Holographic (DH) theory (17-18, incorporated herein by reference in their entirety) discovered by Inventors. The latter is based on representation of systems (physical, biological, cognitive) by events which they generate during some time period which Inventors discovered may be adapted for diagnosis of neuro-psychiatric disorders.

In physics, this approach corresponds to the event-picturing of the universe (19-21, incorporated herein by reference in their entirety). Events are outcomes of measurements or patterns of the outcomes. Bohr repeatedly highlighted the role of phenomenon—the event of the individual outcome of a measurement, as a dot on the photo-emulsion screen in the interference experiment with photons or electrons. Generally, DH-theory is heavily based on the methodology of quantum theory. The latter is treated in the Copenhagen manner, as the epistemic theory delivering to observers knowledge about systems. The quantum microsystems are inapproachable directly and the outcomes of measurements are created in the process of complex interaction between a system, say photon, and a measurement device, say a photodetector.

Although the brain is a macroscopic system, the direct introspection of its mental state is impossible and an observer, say neurophysiologist, psychologist, or psychiatrist, should use various observation techniques, from physical EEG or MRI measurements, or asking a person a variety of questions. (Here asking of a question plays the role of a measurement.) In cognitive studies, it is even more evident (than in quantum physics) that outcomes of mental observables are not "intrinsic properties of human psychic", but events (phenomena in Bohr's meaning) associated with brain's functioning. Inventors discovered that the event approach from physics may be adapted—to study of system's behaviour and use in studies on cognition and human psyche.

Additional details are now described to help understand at least some embodiments. Bohr (the Copenhagen interpretation) and modern quantum information interpretations of quantum mechanics, and/or (Wheeler, 1990, incorporated herein by reference in its entirety) with his "it from bit" program of reconstruction of physics, as well as the methodology of information biology, starting with Johnson (22, incorporated herein by reference in its entirety) who characterized information theory as a "general calculus for biology", may be referred to. Gatenby and Frieden (2007), incorporated herein by reference in its entirety, pointed out: "it is clear that life without matter and energy is impossible, Johnson's manuscript emphasizes that life without information is likewise impossible. Since the article, remarkable progress has been made towards understanding the informational fundament for life.

DH-theory (17, 18) presents a novel realization of aforementioned ideas by using new representation of events, namely, by trees—dendrograms constructed from data with the aid of hierarchic clustering algorithms. For concrete experimental data, trees are finite, but in theoretical considerations, as in (17, 18) infinite trees may be used. The most useful for applications are homogeneous trees with the same number of edges for each vertex; a p-adic tree's structure is characterized by one incoming edge and two outgoing edges for each vertex, here p>1 is a natural number. P-adic trees can be endowed with the algebraic structure, addition, subtraction, multiplication, and, for prime p, even division. The simplest trees are 2-adic ones and at least some embodiments described herein work with clustering processes for generating such trees. A tree can be endowed with ultrametric topology; its distinguishing property is that any two balls are either disjoint or one is sub-ball of another.

P-adic trees endowed with algebra are sometimes known as rings of p-adic numbers (23, incorporated herein by reference in its entirety). They have been widely used in physics, string theory, cosmology, general relativity, quantum theory (24-30). The recent Nobel Prize Laureate G. Parisi used p-adic numbers in the mathematically rigorous formulation of the replica symmetry method playing the fundamental role in theory of complex disordered systems—spin glasses (31-33, incorporated herein by reference in its entirety), see the article of Parisi and Sourlas (34, incorporated herein by reference in its entirety); see also Khrennikov and Kozyrev (35, incorporated herein by reference in its entirety). P-adic trees were also used in biology (36-41, incorporated herein by reference in its entirety), e.g., for modelling of information processing in brain and psychological behaviour (36-39, 42, incorporated herein by reference in its entirety). The crucial step from theoretical modelling to practical applications was done in paper (43, incorporated herein by reference in its entirety); see also patent (44, incorporated herein by reference in its entirety), where the clustering algorithms and generated by them dendrograms were used for representation of hierarchic relations between events—outcomes of EEG-measurements. The technique is based on operation with time series of dendrograms, instead of straightforward operation with time series EEG-outputs. The medical diagnostic approach (43) was based on relatively rough information characteristic of dendrograms—quantum potential. The latter is the basic entity of Bohmian mechanics. Its information interpretation was used in the spirit of Bohm and Hiley (45, incorporated herein by reference in its entirety). It is noted that quantum probability and information are widely used in modelling of cognition, decision making, psychology, social science, see, e.g., (37, 46-49, incorporated herein by reference in its entirety). This approach is known as quantum-like—to distinguish it from genuine quantum physical theory of cognition (in the spirit of Penrose and Hameroff). The specifics of quantum-like model of (43) is the dendrogramic configuration space.

At least some embodiments described herein address the above mentioned technical problem, and/or improve the above mentioned technical field, by providing more precise characterization of patient's mental state, which is referred to herein as a patient's personal universal dendrogramic holographic signature (PUDHS). The PUDHS provides a finer picture of hierarchic interrelation between events generated by the patient's brain (e.g., than was given by quantum potential) and leads to higher efficiency of discrimination between patients in different groups.

At least some embodiments described herein may operate without training a machine learning model. The non-machine learning model approach described herein does not require large training datasets for training a machine learning model. The non-machine learning model approach described herein improves performance of a computing device, by requiring fewer processing resources, is performed in less processing time, and/or requires fewer memory resources, in comparison to training and inference approaches based on machine learning models. However, at least some embodiments may be implemented based on a machine learning model, for example, using the machine learning model to learn the best z, m, and b values, described herein.

The fundamental concept of DH-theory is the "event"—an event can be any measurable, or number of measurable features of the world. For instance, a measurement of a classical particle position, calcium level in blood test or, as in the study described herein—electric potential measured at a patients scalp in one electrode. Each event has a particular relation to any other event measurement of the world. In reference to the previous examples, a particle position is in relation to any other particle position by some pre-chosen distance metric, calcium level in a blood test is in relation for a calcium level in a previous blood test and electric potential from one electrode is in relation to other electric potential measured by the same or other electrodes before and after.

At least some embodiments described herein (e.g., an as described in the study in the "Examples" section) relates to the relations that come about between events measured by EEG. These relations are characterized in order to discriminate between patients group, for example, 3 patient groups as described in the "Examples" section—control patients that have no neurological or psychiatric disease, depressed patients and schizophrenic patients.

At least some embodiments described herein relate to the integration of the holistic brain function embodied in EEG signals with inert hierarchy of the brain signals. At least some embodiments described herein adapt the DH-theory which utilizes dendrogram representation of data as p-adic numbers. By extracting characteristic information patterns from dendrograms expressing the hierarchical treelike structure of information processing in the brain, encoded by p-adic numbers, Inventors successfully differentiate and predict the neuropsychiatric diseases—depression and schizophrenia. Furthermore, AUCs showed high values, thus high accuracy, of differentiating patients with schizophrenia and depression to controls making the individual signatures described in the result and method section a useful tool to identify those neuropsychiatric diseases.

The search for biomarkers that diagnose brain diseases has focused primarily on biological samples, including serum or cerebrospinal fluid (CSF), or on neuroimaging techniques, including e.g., magnetic resonance imaging (MI). These methods are either invasive or expensive and none has yielded an accurate biomarker for diagnosis of heterogenous disorders such as major depression, or schizophrenia (Birur, Kraguljac, Shelton, & Lahti, 2017; Kennis et al., 2020; Strawbridge, Young, & Cleare, 2017; Zhuo et al., 2019, incorporated herein by reference in their entirety). several EEG data analysis techniques have been used in recent research efforts to diagnose psychiatric diseases like schizophrenia (Baradits et al., 2019; Endres et al., 2016; Maran et al., 2016; Oh et al., 2019, incorporated herein by reference in their entirety), and depression (Arns & Gordon, 2014; Newson & Thiagarajan, 2018; Olbrich & Arns, 2013; Wade & Iosifescu, 2016; C.-T. Wu et al., 2018, incorporated herein by reference in their entirety). A machine learning algorithm approach with promising results have been developed by Wu et al., using resting-state EEG to predict treatment responses in major depression (W. Wu et al., 2020, incorporated herein by reference in its entirety). Most studies use of EEG in a special research environment (involving standardized situations, separate open and closed eye conditions, and artefact reduction) with significant reduced applicability to be clinically implemented for screening, diagnosis and prediction.

It is noted that approaches described herein are different than the study of hierarchical/p-adic representation of brain signals described in recent study (43, incorporated herein by reference in its entirety). The study described with reference to (43) has shown promising evidence for the power of hierarchical and topological features of dendrograms, quantified by the p-adic quantum potential, in discrimination of multiple neuropsychiatric diseases including depression, schizophrenia, and cognitive decline (AD and MCI). However, the study described with reference to (43) require a trained machine learning model and it quantifies different topological features of dendrograms. Comparing with quantum potential the patient's dendrogramic signature computed using approaches described herein provides finer characterization of her mental state than quantum potential. The latter is the relatively rough characteristics of relational hierarchy in information representation by the brain. (But even this characteristics is a powerful machinery for quantification of cognition and diagnostic of mental diseases). Moreover, at least some embodiments based on the dendrogramic signature described herein are machine learning free and/or provide a unique range of values to each psychiatric disease or mental state.

Experimental results described in the "Examples" section below indicate that some relations between EEG events may be very abundant in the control patients' signals, less so in the schizophrenic patients and much less frequent in the depressed patients. Thus, the normal brain's functioning may be characterized by significantly higher degree of hierarchical interconnection in information processing than brain's functioning distorted by psychic deviations. Of course, one cannot "come directly into brain's internal world" and therefore requires use of very rough observational picture generated by EEG signals. But, even this rough picture reflects the significant difference on brain's functioning. This comparative medical diagnostic studies can have impact to foundational studies of cognition. These experiments results provide empirical evidence that PUDHS as implemented in at least some embodiments described herein may be used as a quantitative measure of cognition.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1B:
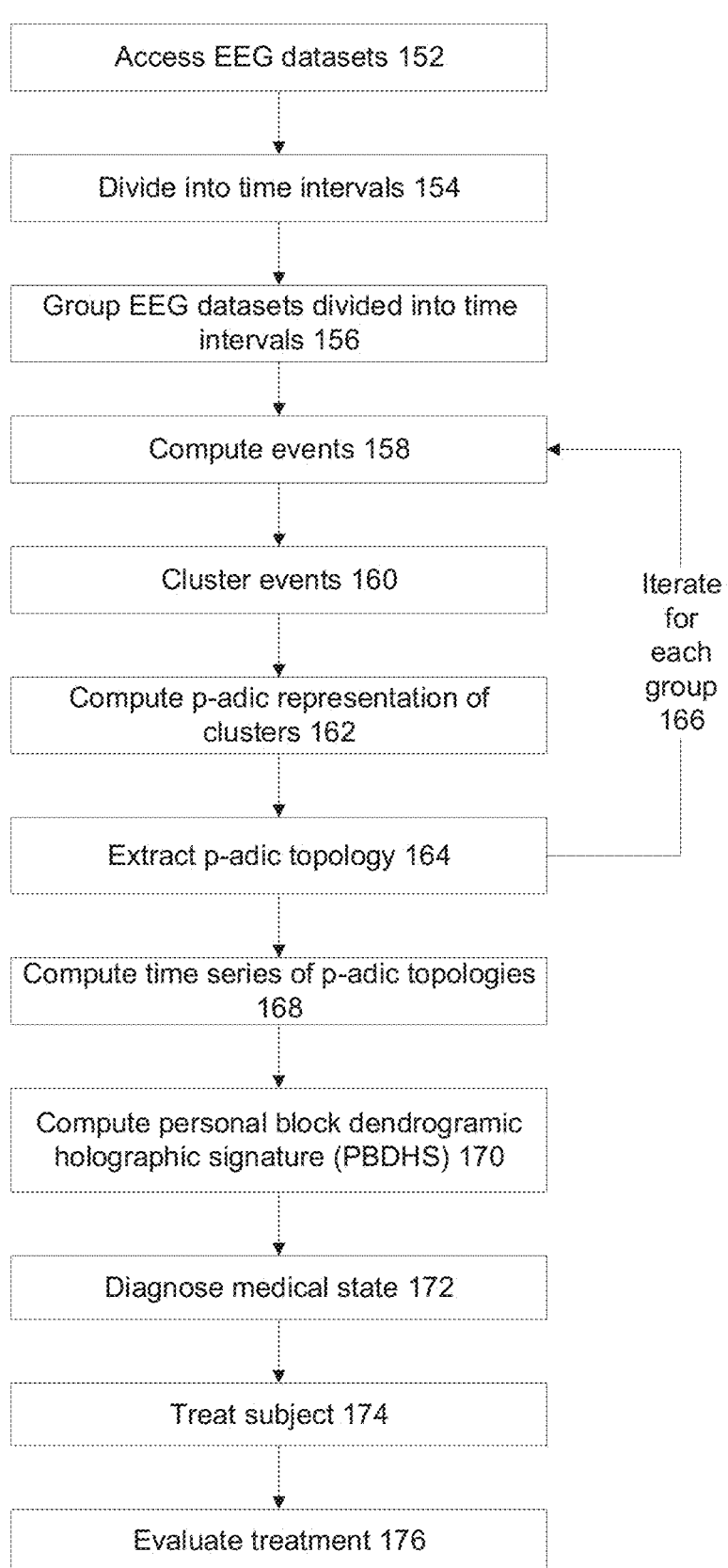
FIG. 1B is a flowchart of a method of computing a personal block DH signature (PBDHS) for a subject, in accordance with some embodiments of the present invention.
Figure 2:
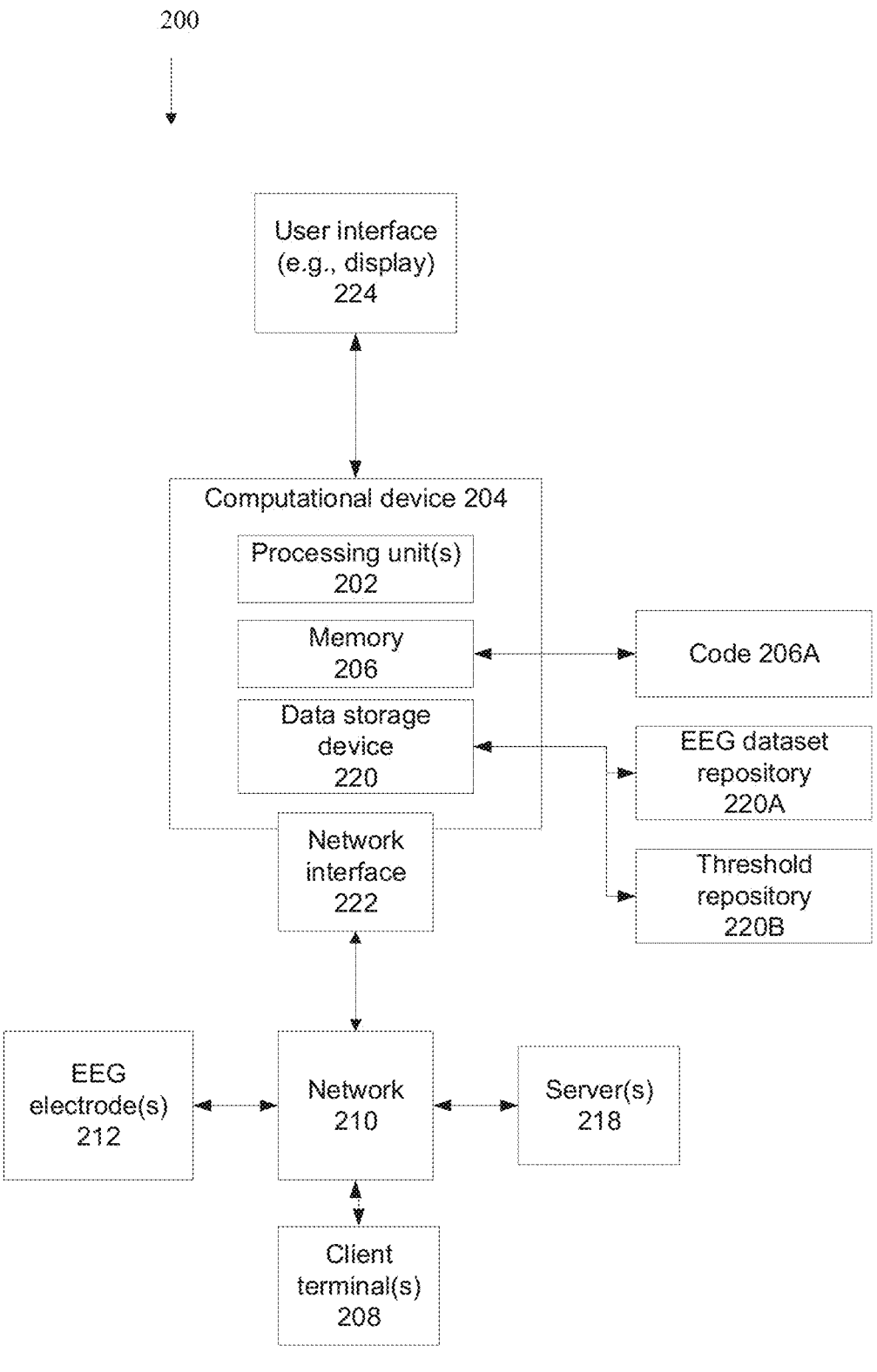
FIG. 2 is a block diagram of components of a system for computing PUDHS and/or PBDHS for a subject, in accordance with some embodiments of the prevent invention.
Figure 3:
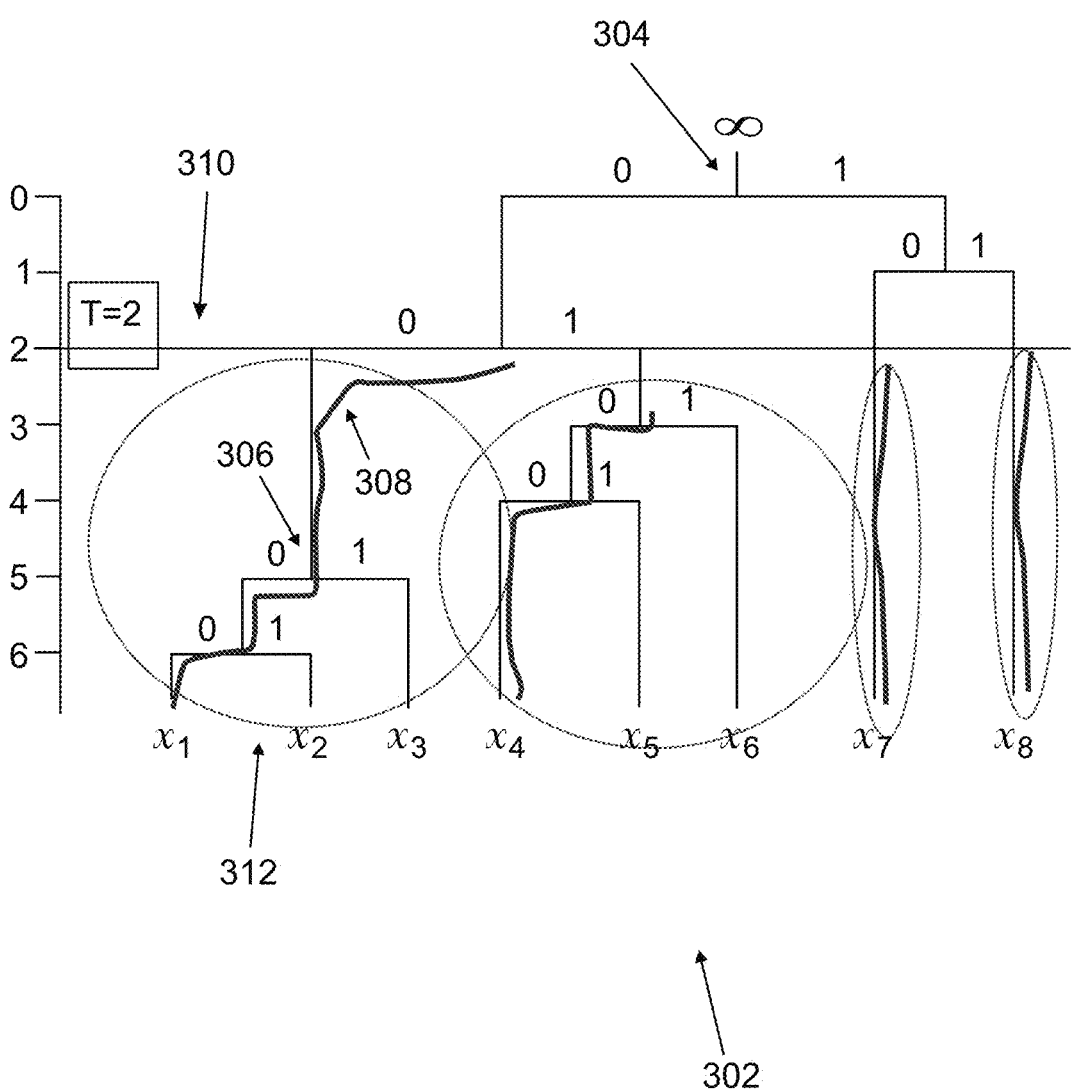
FIG. 3 is a schematic of an example a tree structure called dendrogram representing relations between events under the selection of distance metric and linkage, in accordance with some embodiments of the present invention.
Figure 4:
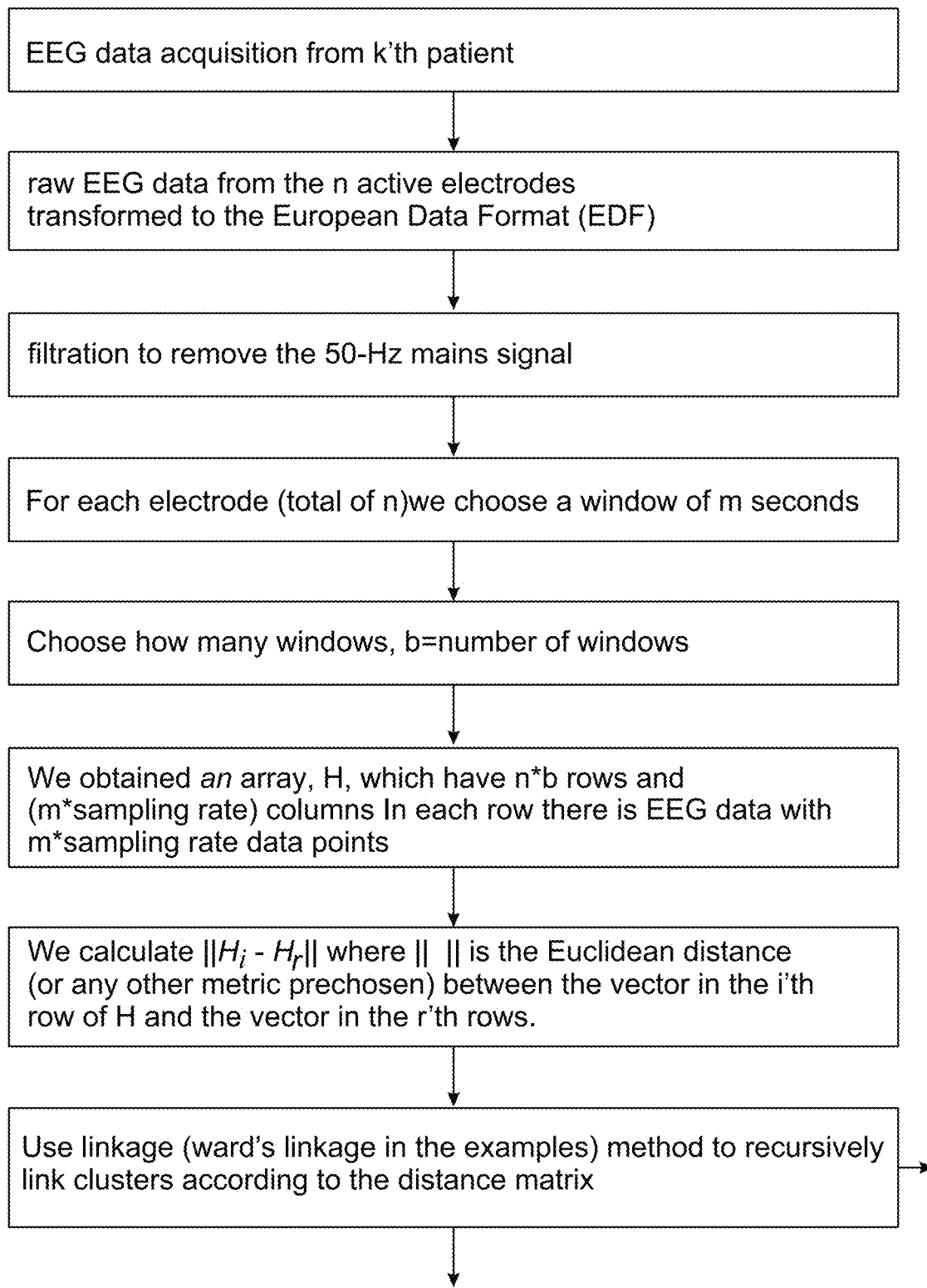
FIG. 4 is a flowchart of an exemplary method of computing PUDHS, in accordance with some embodiments of the present invention.
Figure 5:
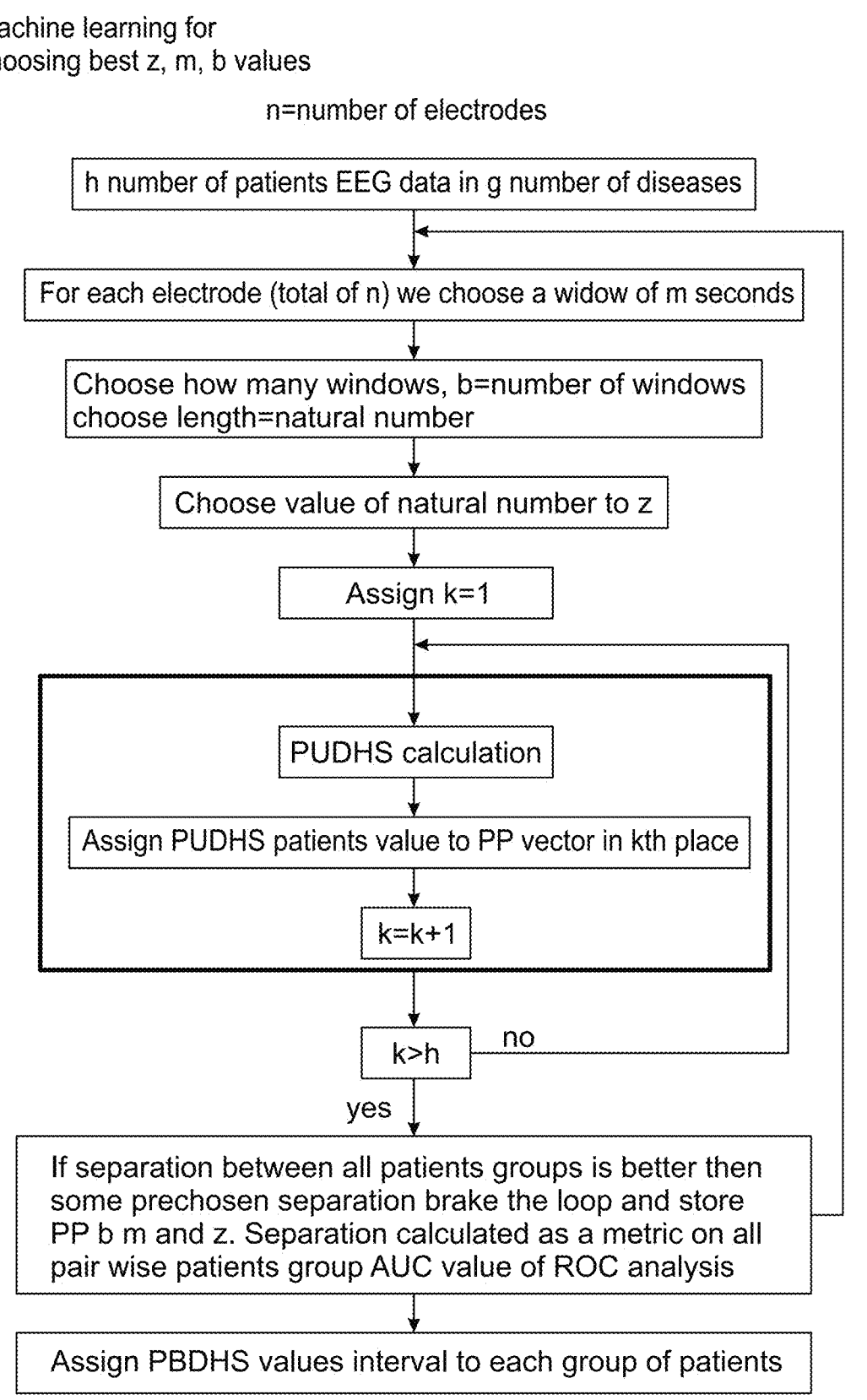
FIG. 5 is a flowchart of an exemplary method of selecting z, m, and b values using machine learning approaches for providing good separation between patient groups for computing the PUDHS values, in accordance with some embodiments of the present invention.
Figure 6:
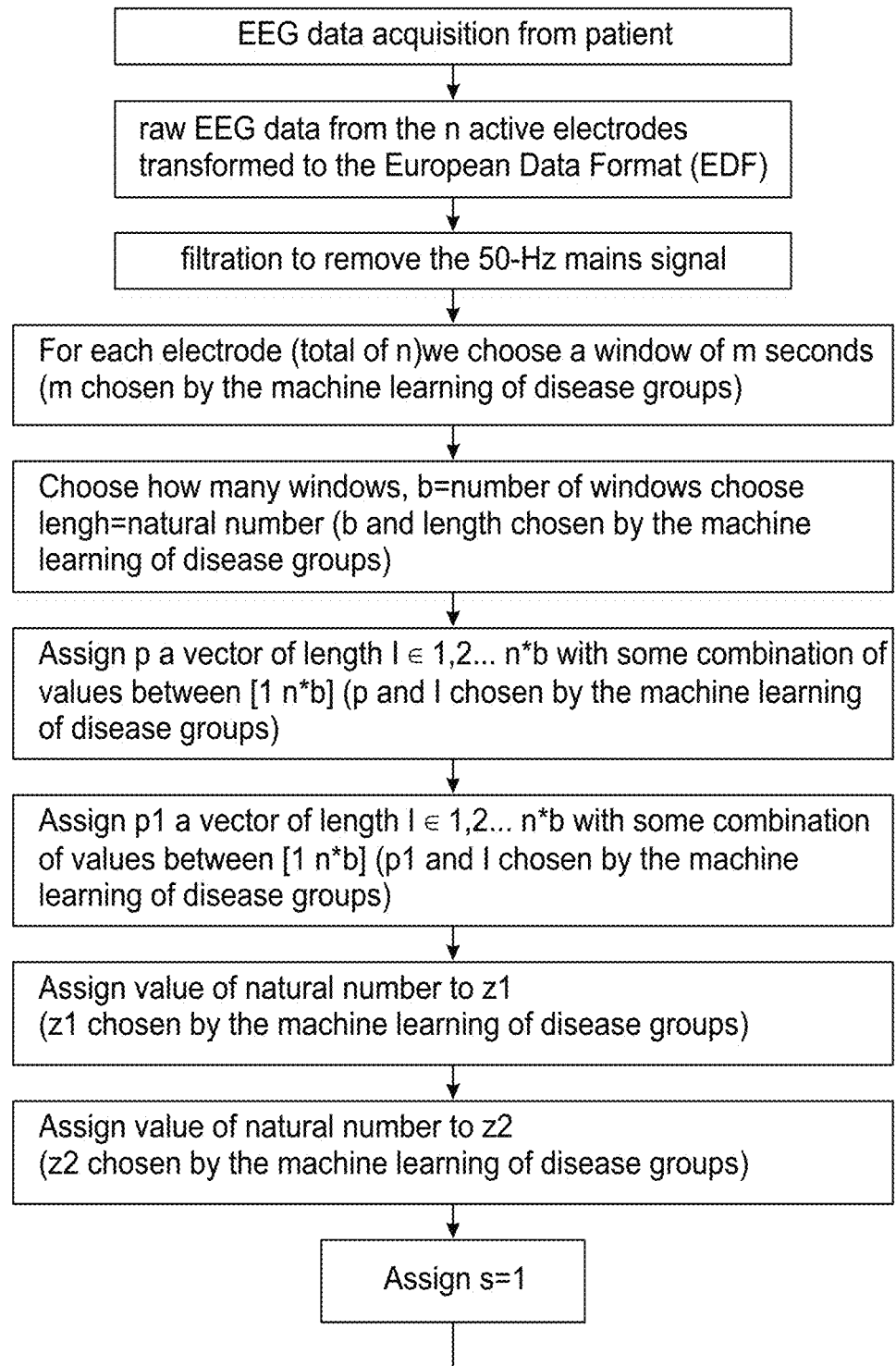
FIG. 6 is a flowchart of a method for computing PBDHS, in accordance with some embodiments of the present invention.
Figure 10:
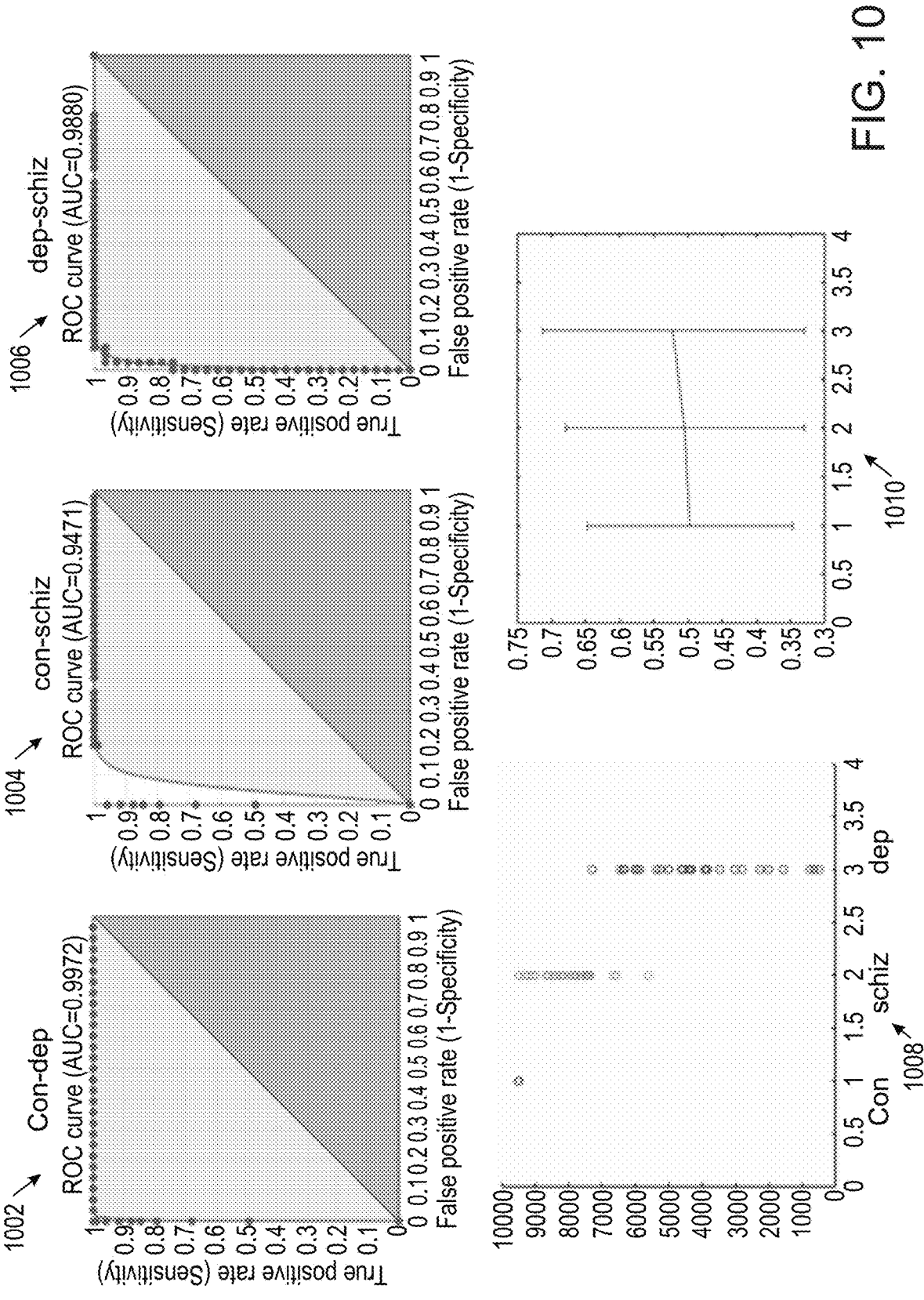
FIG. 10 includes graphs depicting some exemplary results of the experiment conducted by Inventors, in accordance with some embodiments of the present invention.
Figure 11:
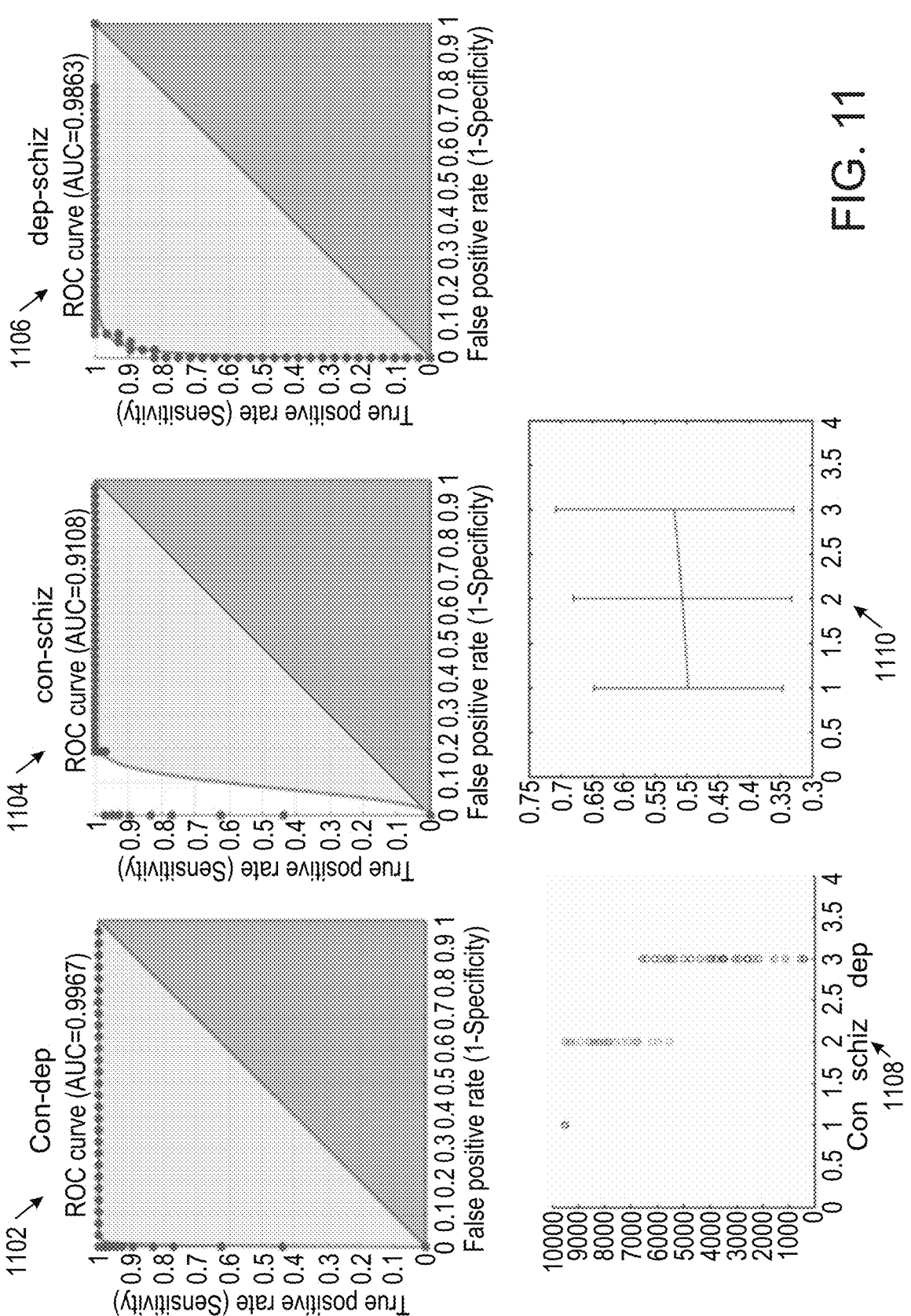
FIG. 11 includes graphs depicting some additional exemplary results of the experiment conducted by Inventors, as described it the "Examples" section below, in accordance with some embodiments of the present invention.
Figure 12:
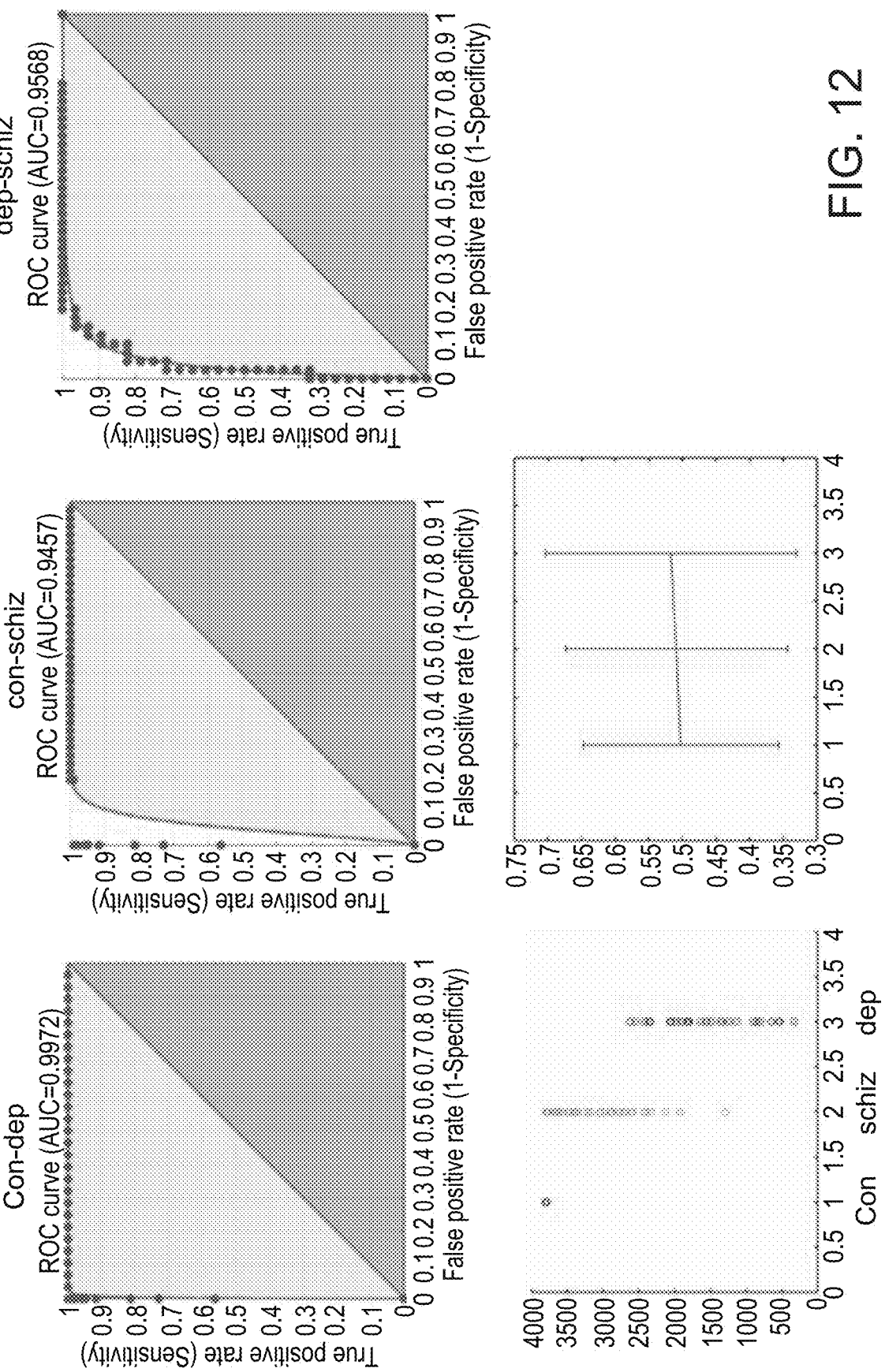
FIG. 12 includes graphs depicting some additional exemplary results of the experiment conducted by Inventors, in accordance with some embodiments of the present invention.
Figure 13:
FIG. 13 includes graphs depicting best results for the 64×1 million runs, in accordance with some embodiments of the present invention.
Figure 13:
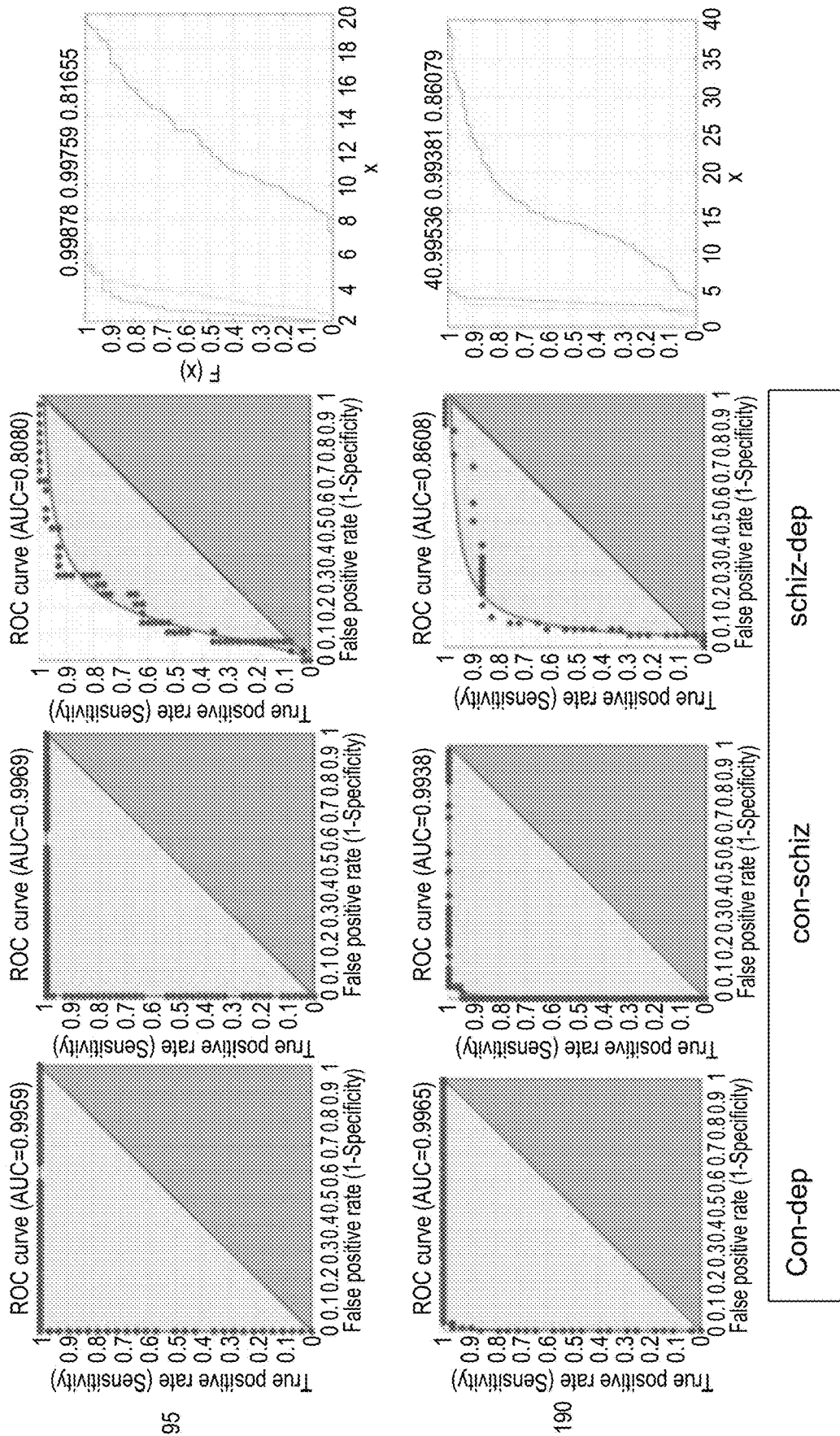

Reference is now made to FIG. 1A, which is a flowchart of a method of computing a personal universal dendrogramic holographic signature (PUDHS) for a subject, in accordance with some embodiments of the present invention. Reference is also made to FIG. 1B, which is a flowchart of a method of computing a personal block DH signature (PBDHS) for a subject, in accordance with some embodiments of the present invention. Reference is also made to FIG. 2, which is a block diagram of components of a system for computing PUDHS and/or PBDHS for a subject, in accordance with some embodiments of the prevent invention. Reference is also made to FIG. 3, which is a schematic of an example a tree structure called dendrogram representing relations between events under the selection of distance metric and linkage, in accordance with some embodiments of the present invention. Reference is also made to FIG. 4, which is a flowchart of an exemplary method of computing PUDHS, in accordance with some embodiments of the present invention. Reference is also made to FIG. 5, which is a flowchart of an exemplary method of selecting z, m, and b values using machine learning approaches for providing good separation between patient groups for computing the PUDHS values, in accordance with some embodiments of the present invention. Reference is also made to FIG. 6, which is a flowchart of a method for computing PBDHS, in accordance with some embodiments of the present invention. Reference is also made to FIG. 7, which is a flowchart of a method for maximizing discrimination levels between groups by performing the PBDHS calculation with different z1 and z2 combinations, in accordance with some embodiments of the present invention. Reference is also made to FIG. 8, which is a flowchart of a method for computing FF and FF1, in accordance with some embodiments of the present invention. Reference is also made to FIG. 9, which is a flowchart of an exemplary method of selecting PP, p, p1, FF, FF1, z1, z2, m, and b values using machine learning approaches for providing separation of patient groups for computation of PBDHS values, in accordance with some embodiments of the present invention. Reference is also made to FIG. 10 which includes graphs depicting some exemplary results of the experiment conducted by Inventors, in accordance with some embodiments of the present invention. Reference is also made to FIG. 11 which includes graphs depicting some additional exemplary results of the experiment conducted by Inventors, as described it the "Examples" section below, in accordance with some embodiments of the present invention. Reference is also made to FIG. 12 which includes graphs depicting some additional exemplary results of the experiment conducted by Inventors, in accordance with some embodiments of the present invention. Reference is also made to FIG. 13 which includes graphs depicting best results for the 64×1 million runs, in accordance with some embodiments of the present invention.

System 200 described with reference to FIG. 2 may implement the features of the method described with reference to FIGS. 1A, 1B, and/or 3-13, by one or more hardware processors 202 of a computing device 204 executing code instructions stored in a memory (also referred to as a program store) 206. The experimental results described with reference to FIGS. 10-13 may be obtained using the approaches described with reference to FIGS. 1A, 1B and/or 3-13 and/or using components of system 200 described with reference to FIG. 2.

Computing device 204 may be implemented as, for example, a client terminal, a server, a virtual machine, a virtual server, a computing cloud, a mobile device, a desktop computer, a thin client, a Smartphone, a Tablet computer, a laptop computer, a wearable computer, glasses computer, and a watch computer.

Multiple architectures of system 200 based on computing device 204 may be implemented:

In an exemplary implementation of a centralized architecture, computing device 204 storing code 206A may be implemented as one or more servers (e.g., network server, web server, a computing cloud, a virtual server) that provides centralized services for computing PUDHS and/or PBDHS and/or diagnosing the medical state according to the PUDHS and/or PBDHS (e.g., one or more of the acts described with reference to FIGS. 1A, 1B, and/or 3-13) to one or more servers 218 and/or client terminals 208 over a network 210, for example, providing software as a service (SaaS) to the servers 218 and/or client terminal(s) 208, providing software services accessible using a software interface (e.g., application programming interface (API), software development kit (SDK)), providing an application for local download to the servers 218 and/or client terminal(s) 208, and/or providing functions using a remote access session to the servers 218 and/or client terminal(s) 208, such as through a web browser and/or viewing application. For example, users use client terminals 208 to access computing device 204 to provide EEG datasets sensed by EEG electrodes monitoring respective heads of subjects.

In another example of a localized architecture, code 206A is obtained from computing device 204, and/or locally executed on client terminal 208 and/or on server 218. For example, a user may use code 206A executing on client terminal 208 to locally computing PUDHS and/or PBDHS and/or for diagnosing the medical state according to the PUDHS and/or PBDHS. For example, each EEG lab and/or each psychiatrist installs a local copy of code 206A on their own computer to locally compute PUDHS and/or PBDHS and/or diagnose subjects.

Computing device 204 receives EEG dataset captured by EEG electrode(s) 212. EEG electrode(s) 212 sense EEG signals of a head of a subject. EEG electrode(s) 212 may be wet and/or dry electrodes. EEG electrode(s) 212 may be standard EEG electrodes arranged in a standard EEG configuration, for example, as used for detecting epilepsy, performing sleep studies, and the like.

EEG electrode(s) 212 may transmit captured EEG datasets (i.e., of EEG signals) to computing device 204, for example, via a direct connected (e.g., local bus and/or cable connection and/or short range wireless connection), and/or via a network 210 and a network interface 222 of computing device 204 (e.g., where EEG electrode(s) are connected via internet of things (IoT) technology and/or are located remotely from the computing device).

Network interface 222 may be implemented as, for example, a wire connection (e.g., physical port), a wireless connection (e.g., antenna), a network interface card, a wireless interface to connect to a wireless network, a physical interface for connecting to a cable for network connectivity, and/or virtual interfaces (e.g., software interface, application programming interface (API), software development kit (SDK), virtual network connection, a virtual interface implemented in software, network communication software providing higher layers of network connectivity).

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may code 206A that execute one or more acts of the method described with reference to FIGS. 1A, 1B and/or 3-13.

Computing device 204 may include data storage device 220 for storing data, for example, EEG dataset repository 220A for storing EEG datasets captured by EEG electrode(s) 212, for example, where each record of the EEG dataset stores multiple EEG datasets obtained from multiple EEG electrodes sensing a head of a respective subject (e.g., simultaneous recordings). Data storage device 220 may store threshold repository 220B which stores different thresholds used to compute the PUDHS and/or PBDHS and/or for diagnosing the medical state. Data storage device 220 may be implemented as, for example, a memory, a local hard-drive, a removable storage unit, an optical disk, a storage device, a virtual memory and/or as a remote server 218 and/or computing cloud (e.g., accessed over network 210).

Computing device 204 and/or client terminal(s) 208 and/or server(s) 218 include and/or are in communication with one or more physical user interfaces 224 that include a mechanism for inputting data (e.g., enter name of subject, select which disorder is being diagnosed) and/or for viewing data, for example, a display for presenting the computed PUDHS and/or PBDHS and/or for presenting the diagnosis. Exemplary user interfaces 224 include, for example, one or more of, a touchscreen, a display, a keyboard, a mouse, and voice activated software using speakers and microphone.

Referring now back to FIG. 1A, at 102, the processor accesses multiple EEG datasets.

EEG datasets (i.e., EEG measurements) are obtained from multiple EEG electrodes monitoring a head of a subject. The EEG datasets may be standard EEG datasets obtained by standard EEG electrodes in standard monitoring locations. Raw EEG data from about 5-30, or 10-25, or about 19 (e.g., as in the Experiment described herein), or other number of active electrodes may be used.

EEG dataset may be obtained with a sampling frequency of for example, 500 hertz (Hz) or another value.

The EEG dataset may be transformed, for example, to European Data Format (EDF).

The EEG data may be filtered to remove an about 50 hertz (Hz) main signal. Further data may be filtered with a high pass filter of, for example, about 1 Hz.

The EEG data may be collected over a sample time interval which may be continuous, for example, about 100-500 seconds, or about 300-400 seconds, or 351 seconds (as in the Experiment described herein).

At 104, the processor computes multiple events for the EEG datasets.

Exemplary events are computed as for example, a vector representation of a respective EEG dataset, and/or a time interval of a selected length of the respective EEG dataset.

The vector representation may be, for example, a digital representation of multiple EEG datasets. The vector representation may be the digital representation of the multiple EEG datasets over a time window, for example, about 1 second, or 5 seconds, or 50 seconds, or 500 seconds, or 1000 seconds, or other values. For example, the vector representation may be the magnitude of the EEG signal, and/or values of the EEG signal in a different domain (e.g., frequency domain), as sampled over the time interval.

At 106, the processor clusters the events into multiple clusters.

Optionally distances between EEG datasets are computed. Each respective distance may be computed for a respective pair of EEG datasets. Distances may be computed, for example, as a Euclidean distance between the EEG datasets (e.g., each EEG dataset is a vector representing a point in Euclidean space). The distance may be stored in a distance matrix.

The clustering may be performed by computing a hierarchical relationship between the distances. For example, recursively linking clusters according to the distance matrix, for example, based on the Ward's linkage approach.

At 108, the processor computes a p-adic representation of the clusters, optionally 2-adic.

The p-adic representation may indicate relative and/or non-absolute relationships between the events.

Optionally, the p-acid representation is computed according to hierarchical relationships computed as described with reference to 106.

Optionally, the p-adic representation is a dendrogram. Each branch of the dendrogram represents a respective event. The dendrogram may include a homogenous tree with a same number of edges for each vertex. Each vertex may include one incoming edge and two outgoing edges. Each branch of the dendrogram may be labeled by a binary number denoting a natural number encoding each respective branch. A set of all branches may be a 2D structure denoting the p-acid topology of the dendrogram. The p-adic representation of each respective branch may encode relations of the respective branch to all other branches. A distance between natural numbers may be denoted by a common root-branch. A longer common root may indicate a shorter distance.

Referring now back to FIG. 3, an example a tree structure called a dendrogram 302 is depicted. The dendrogram represents relations between events under the selection of distance metric and linkage, as described herein.

For example, the dendrogram may be represented by (finite) 2-adic tree: one vertex, its root 304, plays the role of the origin of the 2-adic coordinate system, where each node (e.g., one node 306 is marked for simplicity and clarity) may have one edge coming into it and two edges coming out of it. Branches (e.g., one branch 308 is marked for simplicity and clarity) are pathways combined of edges and going from the root-edge to an edge at the bottom level of the tree. Each branch may be labeled by a binary string of 0 and 1. Such binary string may represent a natural number encoding this branch of the tree (or a point at its bottom level). The set of all branches in the tree is a 2-dimensional structure referred to herein as the dendrogram's topology. One system of branch-labeling known as the prefix-code is described herein. Other approaches to branch-labeling may be used. The distance between natural numbers may be determined by the hierarchic structure of the tree, which is referred to herein as the 2-adic metric. (The distance between two branches may be determined by their common root-branch: longer the common root—shorter the distance, for example, as described herein.)

Referring now back to 108 of FIG. 1A, the 2-adic representation uniquely determines branch i, or rather event i, and relations to all other branches/events. This 2-adic number labeling branch i (event i) is denoted as Vi.

It is to be noted that the absolute magnitudes of EEG-outputs (events) is not used (e.g., excluded), but rather relations between these events are used. The latter are expressed by 2-adic numbers. Each such number represents complex context of special (locations of 19 s electrodes) and temporal dynamics of the brain's state.

Each subject's EEG recording may be represented in the dendrogramic relational hierarchic structure. A time window of 1 second (or 0.5 second, or 2 second) may be used, or other values may be used. Depending on the sample frequency of the EEG recording of that patient, for each of the 19 electrodes, 500 vectors of size 1 s*(frequency of sampling) may be computed (as not necessarily limiting examples, or other values may be used), for example, 500 seconds of recording divided into 19×500 vectors. A matrix of 9500 row vectors is obtained, where each vector represents an "event" with some, yet unknown, relation to all other vectors. In order to extract the relations between these events pairwise distance are calculated between all events (9500*9499/2 such distances). The distances may be, for example, Euclidean distances, or other distances based on a predefined distance metric. These events are linked hierarchically according to their distance with the resulting dendrogramic tree. Each branch of the dendrogram represents an event (a vector of size 1 s*(frequency of sampling)).

Any branch may be represented by a 2-adic expansion that encodes its relation to all other branches (events), where the sum of the 2-adic expansion is a natural number. In this example, 9500 natural numbers which fully represent the dendrogram topology may be obtained.

Referring now back to FIG. 1A, at 110, the processor extracts a p-adic topology from the p-adic representation of the clusters. The p-adic representation may be a p-adic ball.

At 112, the processor computes a personal universal dendrogramic holographic signature (PUDHS) of the p-acid topology, relative to a personalized threshold. The personalized threshold may separate between a relative large distance between events and a relatively small distance between events. The PUDHS may denote a number of events below the personalized threshold.

Referring now back to FIG. 3, line 310 represents the personalized threshold, set at a value of 2.

A threshold that cuts the dendrogram at some level produces disconnected subsystems (sub-dendrograms, marked by circles, where one circle A12 is marked for clarity and simplicity) of the main dendrogram that are connected only in levels that are smaller than the threshold A10, down towards the root of the complete dendrogram. By finding events that are smaller than the threshold the number of such disconnected subsystems with same 2-adic ball radius are counted, which equals to $$r = \text{max padic ball of dendrogram} - \text{treshold ball} \quad (6)$$

Referring now back to FIG. 1A, at 110, the personalized threshold may be computed individually for each subject. The personalized threshold may vary between subjects according to the respective p-adic topology of the respective subject. The personalized threshold may be computed for each session of each subject, i.e., for each set of EEG datasets. Alternatively, the personalized threshold may be computed initially for each subject. The same personalized threshold may be then used for the same subject for different sessions in which different EEG datasets are obtained (e.g., at different days).

The PUDHS may denote a number of branches of the dendrogram smaller than the personalized threshold.

The personalized threshold may be computed as being lower than a maximal p-adic ball of the p-adic topology by a parameter (e.g., denoted z). The parameter may be fixed at a same value for other subjects.

Exemplary details of the personalized threshold and computation of the PUDHS are now described.

The aim may be to characterize each patient's relations between events. To do so, the topological structure of the patient's dendrogram may be characterized. For that purpose, the personalized threshold number is set for example using the following equation (1):

$$T_{personal\ Universal\ dendrogram} = 2^{maximal\ p-adic\ ball\ of\ dendrogram-z} \quad (1)$$

As used herein, the phrase "maximal p-adic ball of dendrogram" or the term "p-adic ball" may be interchanged with the $V_i$ (described herein) with the maximal natural number representation of its p-adic value.

In equation (1) z is a natural number (model's parameter) and may be is set the same for all patients. It is noted that $T_{personalUniversal\ dendrogram}$ may be determined individually for each patient, and may vary between patients, according to its personal universal dendrogram. The number of branches smaller than this threshold are then computed.

The patient's personal universal DH signature (PUDHS) may be mathematically defined as $$PUDHS = \quad (2)$$

number of edges $V_i$ which are smaller than $T_{personal\ Universal\ dendrogram}$ For calculating the PUDHS, for all patients, parameter's value are selected from z=1, 2 . . . 8

Best results (e.g., as shown in FIGS. 10-13 herein) were obtained by Inventors in experiments when z=8, but may vary according to subjects and/or medical states being evaluated.

At 114, the processor may compute a diagnosis of the medical state associated with the neuro-psychiatric disorder according to the PUDHS, relative to a medical threshold that separates between presence of the medical state and non-presence of the medical state.

The medical threshold that separates between presence of the medical state and non-presence of the medical state may be set by: computing multiple PUDHS values. Each PUDHS value is computed for one of multiple subjects associated with an indication (e.g., label, tag) of the medical state or an indication of non-presence of the medical state, using respective EEG datasets. The medical threshold is set to separate between PUDHS values of subjects associated with the indication of the medical state, and PUDHS values of subjects associated with the indication of non-presence of the medical state.

Exemplary medical states include one or more of: depression, schizophrenia, Alzheimer's disease (AD), and mild cognitive impairment (MCI). Exemplary non-presence of the medical state include one or more of: no neuro-psychiatric disorder, and another neuro-psychiatric disorder that is different from the medical state.

In another set of examples, the medical state includes stable AD, and/or stable MCI. The non-presence of the medical state may include deteriorating AD and/or deteriorating MCI.

In another example, the medical state includes a prediction of likelihood of developing the neuro-psychiatric disorder in the future, and the non-presence of the medical state includes a prediction of likelihood of not developing the neuro-psychiatric disorder in the future.

In yet another example, the medical state includes a prediction of likelihood of positively clinically significantly responding to a certain treatment for the neuro-psychiatric disorder, and the non-presence of the medical state includes a prediction of likelihood of no clinically significant response to the certain treatment for the neuro-psychiatric disorder.

At 116, the subject (e.g., patient) may be treated using a treatment effective for the medical state. For example, one or more of: psychotherapy, anti-depressant medication, anti-psychotic medication, electroconvulsive therapy (ECT), naturopathic medications, alternative therapies (e.g., acupuncture) and transcranial magnetic stimulation (TMS).

At 118, the applied treatment may be evaluated. For example, the processor computes a first PUDHS value for the subject prior to administration of a certain treatment for the neuro-psychiatric disorder, as described with reference to 102-112. The certain treatment is administered to the subject, for example, as described with reference to 116. The processor computes a second PUDHS value for the subject after the administration of the certain treatment for the neuro-psychiatric disorder, as described with reference to 102-112. A clinically significant response to the certain treatment may be determined, for example, when the second PUDHS value is statistically significantly different from the first PUDHS value.

Referring now back to FIG. 4, a flowchart of an exemplary method of computing PUDHS for a single patient, is provided. The method described with reference to FIG. 4 may represent a more details example, based on the method described with reference to FIG. 1A. One or more features described with reference to FIG. 4 may be based on, combined with, replaced by, and/or included in, the method described with reference to FIG. 1A. One or more features described with reference to FIG. 1A may be based on, combined with, replaced by, and/or included in, the method described with reference to FIG. 4.

Referring now back to FIG. 5, a flowchart of an exemplary method of selecting z, m, and b values (e.g., using machine learning approaches) for providing good separation between patient groups for computing the PUDHS values, is provided. The value z is described with reference to 112 of FIG. 1A, and used in FIG. 4. The values m and b are used in FIG. 4.

Referring now back to FIG. 1B, the notion of a relational system may be defined as a dendrogram with fixed block size which consists of smaller event number than the number of all the acquired events. Thus, a smaller dendrogram with 19 branches that represents relations between 1 s events in all 19 electrodes may be constructed (or other number of branches according to the number of electrodes used). In that way a time series of smaller dendrograms may be constructed, where each branch is represented by the p-adic number denoted Vi. Inventor's main motivation for such analysis is to show that different patient groups produce different relational systems. Such dendrogramic time series with is (as a not necessarily limiting example, or other value may be used) window vector for each electrode defined as an event may be constructed. Thus, we analyzed the time series of 500 dendrograms for each patient (as a not necessarily limiting example, or other value may be used).

At 152, EEG datasets of a subject are accessed, for example, as described with reference to 102 of FIG. 1A.

At 154, the processor divides the EEG datasets into multiple time intervals. The size of the time interval may be selected, for example, based on trial and error using experimental data, based on heuristic approaches, and/or based on machine learning approaches. Examples time intervals are, for example, about 1-1000 seconds, or about 10-750 seconds, or about 100-500 seconds, or other values.

At 156, the processor groups the EEG datasets which are divided into time intervals into multiple groups. Each group includes divided EEG datasets obtained during a common time interval.

Features 158-164 are performed for each group, sequentially and/or in parallel.

At 158, the processor computes events, for example, as described with reference to 104 of FIG. 1A.

At 160, the processor clusters the events into clusters, for example, as described with reference to 106 of FIG. 1A.

At 162, the processor computes a p-adic representation of the clusters, for example, as described with reference to 108 of FIG. 1A.

At 164, the processor extracts a p-adic topology from the p-adic representation of the clusters, for example, as described with reference to 110 of FIG. 1A.

At 166, features described with reference to 158-164 are iterated for each group, sequentially and/or in parallel.

At 168, the processor computes a time series of multiple p-adic topologies. Each respective p-adic topology is computed for each respective group, as described herein by iterating features described with reference to 158-164.

At 170, the processor computes a personal block DH signature (PBDHS) of the time series of the p-adic topologies relative to a first personalized threshold and a second personalized threshold.

The first personalized threshold may be computed for each respective p-adic topology of the time series. The first personalized threshold may separate between a relative large distance between events of the respective p-adic topology and a relatively small distance between events of the p-adic topology.

The first personalized threshold for a respective p-adic topology may be computed as being lower than a maximal p-adic ball of the respective p-adic topology by a first parameter (denoted z1) fixed at a same value for the other p-adic topologies of other subjects.

The second personalized threshold may be computed for all p-adic topologies of the time series. The second personalized threshold may separate between a relative large distance between events of the p-adic topologies of the time series and a relatively small distance between events of the p-adic topologies of the time series.

The second personalized threshold for a respective p-adic topology may be computed as being lower than a maximal p-adic ball of the p-adic topologies of the time series by a second parameter (denoted z2). The second parameter may be fixed at a same value for the other p-adic topologies of other subjects.

Alternatively, the first personalized threshold and the second personalized threshold may be computed as being lower than a maximal p-adic ball of the p-adic topology by a parameter, where the parameter is fixed at a same value for other subjects.

The first personalized threshold and the second personalized threshold may be computed individually for each subject. The first personalized threshold and the second personalized threshold may vary between subjects according to the respective p-adic topology of the respective subject. The first personalized threshold and the second personalized threshold may be computed for each session of each subject, i.e., for each set of EEG datasets. Alternatively, the first personalized threshold and the second personalized threshold may be computed initially for each subject. The same personalized thresholds may be then used for the same subject for different sessions in which different EEG datasets are obtained (e.g., at different days).

Exemplary details of the first and second personalized thresholds and computation of the PBDHS are now described.

In order to characterize the topology of "systems of relations" in each patient, two thresholds (denoted herein as the first personalized threshold and the second personalized threshold) may be used as follows:

The intra system threshold (denoted herein as the first personalized threshold) may be denoted as $$T_{dendrogram} = 2^{maximal\ p-adic\ ball\ of\ a\ particular\ block\ dendrogram\ in\ time\ series - z1} \quad (3)$$

where the model parameter z1 is a natural number and it may be set the same for all patients.

This z1 is a parameter that sets the $T_{dendrogram}$ p-adic ball level lower than the dendrogram ball and is equal to all dendrograms in all patients (method for searching the best z1 value is described herein.

It is noted that the threshold $T_{dendrogram}$ may be determined individually for each patient and each dendrogram (relational block sub-system) of that patient.

The inter threshold (denoted herein as the second personalized threshold) may be defined as follows:

$$T1_{dendrogram} = 2^{maximal\ p-adic\ ball\ of\ all\ block\ dendrograms\ in\ time\ series - z2} \quad (4)$$

where the model parameter z2 is a natural number and it may be set the same for all patients (method for searching the best z2 value is described herein). It is noted that the threshold $T1_{dendrogram}$ may be determined for each patient, and may vary between patients, according to its set of its relational block sub-systems. The intra dendrogram threshold of a patient $T_{dendrogram}$ may be different and may be determined by the concrete block dendrogram of the patient. Thus, each dendrogram in the dendrogramic time series may be associated with a mark number (denoted E) which may be assigned a value from [1 19](or other range according to the EEG electrodes), that indicated how many branches are smaller than threshold $T_{dendrogram}$. Each dendrogram in the time series may be associated with a mark number (denoted E1) which is assigned a value from [1 19](or other range according to the EEG electrodes), that indicated how many branches where smaller then $T1_{dendrogram}$. For each value n=[1 19], a histogram denoted F may be constructed with bins centered at 1, 2 . . . n, where each bin may count how many systems had a mark E with the value of the bin center. The same histogram may be constructed for the E1 marks (as described herein). The h bin centers, p, and h bin centers, p1, may be randomly selected or selected using other approaches.

The patient's personal block DH signature (PBDHS) may be calculated as follows $$PBDHS = \quad (5)$$

$$\max\left((F(p) + 1) * (F1(p1) + 1)\right)/\text{mean}\left((F(p) + 1) * (F1(p1) + 1)\right)$$

This procedure enables combining into one signature score, i.e. the PBDHS, two different thresholds (inter and intra thresholds, i.e., the first and second personalized threshold). Each threshold reveals different features in different p-adic order level of the the block dendrograms.

For each patient, the PBDHS for the first 500 s of an EEG data acquisition with 19 electrode head set may be calculated (as a not necessarily limiting example, or other value). For calculating the PBDHS, each selection of the two parameters z1 and z2 may be tested, where z1=1, 2 . . . 8 and z2=1, 2 . . . 8, thus 64 possible parameters combinations. For each combination of z1 and z2 Inventors selected randomly 1 million times p and p 1 bines, but other values may be used.

At 172, the processor may compute a diagnosis of the medical state associated with the neuro-psychiatric disorder according to the PBDHS, relative to a medical threshold that separates between presence of the medical state and non-presence of the medical state.

The medical threshold that separates between presence of the medical state and non-presence of the medical state may be set, for example by: computing multiple PBDHS values. Each PBDHS value is computed for one of multiple subjects associated with an indication (e.g., tag, label) of the medical state or an indication of non-presence of the medical state, using respective EEG datasets. The medical threshold is set to separate between PBDHS values of subjects associated with the indication of the medical state, and PBDHS values of subjects associated with the indication of non-presence of the medical state.

Exemplary medical states are described, for example, with reference to 114 of FIG. 1A.

At 174, the subject may be treated, for example, as described with reference to 115 of FIG. 1A.

At 176, the applied treatment may be evaluated. For example, the processor computes a first PBDHS value for the subject prior to administration of a certain treatment for the neuro-psychiatric disorder, as described with reference to 152-170. The certain treatment is administered to the subject, for example, as described with reference to 174. The processor computes a second PBDHS value for the subject after the administration of the certain treatment for the neuro-psychiatric disorder, as described with reference to 152-170. A clinically significant response to the certain treatment may be determined, for example, when the second PBDHS value is statistically significantly different from the first PBDHS value.

Referring now back to FIG. 6, a flowchart of an exemplary method for computing PBDHS is provided. The method described with reference to FIG. 6 may represent a more details example, based on the method described with reference to FIG. 1B. One or more features described with reference to FIG. 6 may be based on, combined with, replaced by, and/or included in, the method described with reference to FIG. 1B. One or more features described with reference to FIG. 1A may be based on, combined with, replaced by, and/or included in, the method described with reference to FIG. 6.

Referring now back to FIG. 7, a flowchart of an exemplary method of maximizing discrimination levels between groups by performing the PBDHS calculation with different z1 and z2 combinations, is provided.

Referring now back to FIG. 8, a flowchart of a method for computing values for FF and FF1 used in the method described with reference to FIG. 7, is provided.

Referring now back to FIG. 9, a flowchart of an exemplary method of selecting PP, p, p1, FF, FF1, z1, z2, m, and b values (e.g., using machine learning approaches) for providing separation of patient groups for computation of PBDHS values, is described. The value z1 is the first personalized threshold and the value z2 is the second personalized threshold, as described herein.

The values PP, p, p1, FF, FF1, m, and b, are used in FIGS. 6, 7, and/or 8.

Various embodiments and aspects of the present invention as delineated hereinabove and as claimed in the claims section below find experimental and/or computational support in the following examples.

EXAMPLES

Reference is now made to the following examples, which together with the above descriptions illustrate at least some implementations of systems, methods, apparatus, and/or code instructions described herein.

Inventors conducted an experiment, which was designed and carried out following the guidelines of the Declaration of Helsinki and approved by the local ethics committees of the Rabin Medical Center, Petach Tikva, Israel, and Geha Mental Health Center, Petach Tikva, Israel.

Composition of the Patient Groups

Inventors used the online medical health records of the Rabin Medical Center to identify all patients that underwent at least one routine EEG examination at the Rabin Medical Center between 2011 and 2019. Inventors classified the patients into the following groups:

1) Depression: Patients with a diagnosis of major depressive disorder (MDD) by the Structured Clinical Interview for DSM-IV Axis I Disorders (SCID) of at least moderate depression severity, a major depressive episode beginning before age 30, and either a chronic recurrent episode or recurrent major depressive disorder (average age: 69.7±14.8 years; range: 33-91 years; 20 females).

2) Schizophrenia: diagnosis of schizophrenia according to the International Classification of Diseases (ICD-10) and currently treated at the Geha Mental Health Center, Petach Tikva, Israel.

3) Control: patient undergoing routine EEG due to indications not related to neuropsychiatric diseases. None of the patients in this group was diagnosed with any of the conditions that define the other groups and patients with any of the following additional neuropsychiatric diseases and conditions were excluded: bipolar disorder; substance abuse; psychiatric or general medical conditions requiring hospitalization; history of epilepsy or condition requiring an anticonvulsant, ECT, vagal nerve stimulation, or transcranial magnetic stimulation (TMS); history of TBI; and history or imaging findings of cerebrovascular diseases including ischaemic and haemorrhagic stroke.

EEG Data Acquisition

Routine EEG recordings were retrospectively obtained from the records of all patients. EEG was performed in a routine clinical setting by an experienced technician. All included patients underwent EEG in the hours between 8 am and 1 pm using a Nihon Koden surface EEG (19-electrode standard according to the international 10-20 electrode placement system) with a sampling frequency of 500 Hz (Nihon Kohden, Japan). Patients were resting with open and closed eyes and sleep EEG were excluded.

In order to extract the hierarchical relational dendrogram from patient's EEG signals, first raw EEG data from the 19 active electrodes (elec) were transformed to the European Data Format (EDF) and filtered to remove the 50 Hz main signal. Data were further filtered with a high-pass filter of 1 Hz.

Universal dendrogram analysis and calculation of patient's personal universal DH signature (PUDHS) was performed as described herein, using the following details. For each electrode (total of 19) Inventors chose a window of is which consists 500/200 data points Inventors also chose how many seconds (500/200) will be included in the Universal dendrogram. Each personal Universal dendrogram was constructed by pairwise distances (e.g., Euclidean norm) between all 1 second windows of the 19 electrodes. Then a wards linkage process was employed with the resultant single personal Universal dendrogram $D_{universal}$.

For each patient universal dendrogram, $D_{universal}$ Inventors calculated for each branch the sum of its p-adic expansion:

$$V_r = \sum_{j=0}^{k} a_j \times 2^j, \text{ where } a_j = 1, 0.$$

Thus $V_r$ is a natural number which uniquely represents $event_i$ relation to all other $event_j$ $j \neq i$ for each personal Universal dendrogram Inventors set a threshold $T_{personal\ Universal\ dendrogram}$ Where $[maximal\ p{-}adic\ ball\ of\ dendrogram = log_2(max\ Vi\ of\ dendrogram))]$ And the patient's personal universal DH signature (PUDHS) is given by the quantity:

PUDHS=number of edges,$V_i$,smaller then $T_{personal\ Universal\ dendrogram}$

Block dendrogram analysis and calculation of patient's personal block DH signature (PBDHS) was computed as described herein, using the following details. For each electrode (total of 19) Inventors chose a window of is which consisted of 500/200 data points. Furthermore Inventors chose how many windows/seconds will be included in the dendrogram (1,3,5,10). Inventors then created a dendrogram from these 19,57,95 or 190 windows. Each such dendrogram is constructed by pairwise distances (e.g., Euclidean norm) between all 1 second windows of the 19 electrodes. Then the ward's linkage process was employed with the resultant single dendrogram of 19,57,95 or 190 branches. For each patient Inventors analyzed in this way 500 s which in the different block dendrogram size amount to a time series of 500, 167, 100 or 50 dendrograms. For a particular dendrogram block size Inventors obtain the patient's personal block DH signature as follows:

each dendrogram, $D_i$, where i=1, 2 . . . n n=number of block dendrograms in the dendrogramic time series (in calculations, n=500,167,100,50), consists of j=1, 2 . . . m number of edges (in calculations, m=19,57,95,190)

For each branch sum of its p-adic expansion the following was computed:

$$V_r = \sum\nolimits_{j=0}^{k} a_j \times 2^j, \text{ where } a_j = 1, 0.$$

Thus $V_r$ is a natural number which uniquely represents event$_i$ relation to all other event$_j$ j≠i Thus, Inventors have n, natural numbers $V_r$ vectors, of size m that represent each dendrogram $D_i$ topology For each of the vectors Inventors set two thresholds $T_{dendrogram}$ and $T1_{dendrogram}$ (see equation 3 and 4). The p-adic ball value of each dendrogram was calculated as $\lfloor(\log_2 (\max Vi \text{ of dendrogram}))\rfloor$ from which $T_{dendrogram}$ was set to each dendrogram The maximal p-adic ball value of all dendrograms was calculated as $\lfloor(\log_2(\max Vi \text{ from all dendrograms in the patient time series}))\rfloor$ from which $T1_{dendrogram}$ was set to all dendrograms Inventors calculated for each patient the PBDHS (equation 5).

In order to maximize the discrimination levels between groups, Inventors performed the PBDHS calculation with different z1 and z2 combinations. For each such combination Inventors chose randomly 1 million times different p and p1 bins out of the full histograms F and F1, respectively. Thus, 64×3 million (3 different pair of groups). ROC AUC values between pairs of patient groups PBDHS were calculated. The sum of the three AUC values for each run was calculated and the graphs in FIG. 13 show the run that maximizes this sum.

Results

Referring now back to FIG. 10, graphs 1002, 1004, 1006, 1008, and 1010 depicting some exemplary results of the experiment conducted by Inventors, are presented.

When examining the PUDHS values between the patients of the three groups, Inventors witnessed a very good segregation of values which corresponded to their clinical situation (FIGS. 10, graphs 1002, 1004, 1006). Moreover, when Inventors scrambled the groups randomly the segregation values were significantly smaller (1008, 1010). As can be seen the figures the PUDHS values form a spectrum with sections of the spectrum exclusively belong to each clinical situation.

Furthermore, Inventors verified that the differences in topology of the dendrograms, which at the end represents relations between events, is stable upon shifting the starting time of the analysis.

Referring now back to FIG. 11, graphs 1102, 1104, 1106, 1108, and 1110 depicting some additional exemplary results of the experiment conducted by Inventors, are presented. When 500 s of events were used of each patient, where the 500 s of events started 200s after the beginning of the EEG recording (as a not necessarily limiting example, or other value may be used), Inventors obtained similar segregation values between the 3 groups.

Another question was whether the overall size of the dendrogram can be adapted and whether smaller dendrogram (or smaller number of events) can be used.

Referring now back to FIG. 12, graphs depicting some additional exemplary results of the experiment conducted by Inventors, are presented. The results of FIG. 12 indicate that when used, for each patient, only 200 s of events of the EEG recording, similar segregation values between the 3 groups are obtained.

Reference is now made to FIG. 13, which includes graphs depicting best results for the 64×1 million runs, in accordance with some embodiments of the present invention. Moreover the calculations described herein for Dendrogramic time series were computed with changing dendrogram size/number of branches, (57, 95 and 190 branches which produce a time series of 167,100 and 50 dendrograms, as a not necessarily limiting example, or other value may be used). FIG. 5 depicts the best results of 64×1 million runs for each of the different block size dendrogram sequence (where p and p1 have both the size m).

The first column denotes Con-dep, the second column denotes con-schiz, and the third column denotes schiz-dep.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant EEG datasets will be developed and the scope of the term EEG dataset is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

1. Livingston, G., Sommerlad, A., Orgeta, V., Costafreda, S. G., Huntley, J., Ames, D., . . . Mukadam, N. (2017). Dementia prevention, intervention, and care. *Lancet*, 390 (10113), 2673-2734. doi:10.1016/S0140-6736(17) 31363-6
2. Malhi, G. S., & Mann, J. J. (2018). Depression. *Lancet*, 392(10161), 2299-2312. doi:10.1016/s0140-6736(18) 31948-2
3. Owen, M. J., Sawa, A., & Mortensen, P. B. (2016). Schizophrenia. *Lancet*, 388(10039), 86-97. doi:10.1016/ s0140-6736(15)01121-6

4. Collins, P. Y., Insel, T. R., Chockalingam, A., Daar, A., & Maddox, Y. T. (2013). Grand challenges in global mental health: integration in research, policy, and practice. *PLoS Med*, 10(4), e1001434. doi:10.1371/journal.pmed.1001434
5. Keynejad, R. C., Dua, T., Barbui, C., & Thornicroft, G. (2018). WHO Mental Health Gap Action Programme (mhGAP) Intervention Guide: a systematic review of evidence from low and middle-income countries. *Evid Based Ment Health*, 21(1), 30-34. doi:10.1136/eb-2017-102750
6. Cervenka, M. C., & Kaplan, P. W. (2016). Epilepsy. *Semin Neurol*, 36(4), 342-349. doi:10.1055/s-0036-1585100
7. Smith, S. J. (2005). EEG in the diagnosis, classification, and management of patients with epilepsy. *J Neurol Neurosurg Psychiatry*, 76 Suppl 2, ii2-7. doi:10.1136/ jnnp.2005.069245
8. Baradits, M., Kakuszi, B., Balint, S., Fullajtar, M., Mod, L., Bitter, I., & Czobor, P. (2019). Alterations in resting-state gamma activity in patients with schizophrenia: a high-density EEG study. *Eur Arch Psychiatry Clin Neurosci*, 269(4), 429-437. doi:10.1007/s00406-018-0889-z
9. Endres, D., Perlov, E., Feige, B., Fleck, M., Bartels, S., Altenmuller, D. M., & Tebartz van Elst, L. (2016). Electroencephalographic findings in schizophreniform and affective disorders. *Int J Psychiatry Clin Pract*, 20(3), 157-164. doi:10.1080/13651501.2016.1181184
10. Maran, M., Grent-'t-Jong, T., & Uhlhaas, P. J. (2016). Electrophysiological insights into connectivity anomalies in schizophrenia: a systematic review. *Neuropsychiatric Electrophysiology*, 2(1). doi:10.1186/s40810-016-0020-5
11. Oh, S. L., Vicnesh, J., Ciaccio, E. J., Yuvaraj, R., & Acharya, U. R. (2019). Deep Convolutional Neural Network Model for Automated Diagnosis of Schizophrenia Using EEG Signals. *Applied Sciences*, 9(14). doi: 10.3390/app9142870
12. Arns, M., & Gordon, E. (2014). Quantitative EEG (QEEG) in psychiatry: diagnostic or prognostic use? *Clin Neurophysiol*, 125(8), 1504-1506. doi:10.1016/ j.clinph.2014.01.014
13. Newson, J. J., & Thiagarajan, T. C. (2018). EEG Frequency Bands in Psychiatric Disorders: A Review of Resting State Studies. *Front Hum Neurosci*, 12, 521. doi:10.3389/fnhum.2018.00521
14. Olbrich, S., & Arns, M. (2013). EEG biomarkers in major depressive disorder: discriminative power and prediction of treatment response. *Int Rev Psychiatry*, 25(5), 604-618. doi:10.3109/09540261.2013.816269
15. Wade, E. C., & Iosifescu, D. V. (2016). Using Electroencephalography for Treatment Guidance in Major Depressive Disorder. *Biol Psychiatry Cogn Neurosci Neuroimaging*, 1(5), 411-422. doi:10.1016/ j.bpsc.2016.06.002
16. Wu, C.-T., Dillon, D., Hsu, H.-C., Huang, S., Barrick, E., & Liu, Y.-H. (2018). Depression Detection Using Relative EEG Power Induced by Emotionally Positive Images and a Conformal Kernel Support Vector Machine. *Applied Sciences*, 8(8). doi:10.3390/app8081244
17. Shor O, Benninger F, Khrennikov A. Representation of the Universe as a Dendrogramic Hologram Endowed with Relational Interpretation. *Entropy*. 2021; 23(5):584. www (dot)doi(dot)org/10(dot)3390/e23050584
18. Shor O, Benninger F, Khrennikov A. Dendrogramic Representation of Data: CHSH Violation vs. Nonergodicity. *Entropy*. 2021; 23(8):971. www(dot)doi(dot)org/10 (dot)3390/e23080971

19. Smolin, L. *Einstein's Unfinished Revolution: The Search for What Lies beyond the Quantum*; Penguin Press: London, U K, 2019.

20. Smolin, L. The dynamics of difference. *Found. Phys.* 2018, 2, 643-653.

21. Barbour, J.; Smolin, L. Extremal variety as the foundation of a cosmological quantum theory. *arXiv* 1992, arXiv:hep-th/9203041

22. Johnson, H. A. Information theory in biology after 18 years. Science 1970, 168, 1545-1550.

23. Schikohof, W. H. Ultrameric Calculus. Introduction to p-adic analysis. Cambridge Cambridge Univ. Press, 2010.

24. Volovich, I. V. p-adic string. *Classical and Quantum Gravity,* 1987, 4, 83-87.

25. Vladimirov, V. S.; Volovich, I. V.; Zelenov, E. I. *p-Adic Analysis and Mathematical Physics*; World Scientific: Singapore, 1994.

26. Khrennikov, A. *p-Adic Valued Distributions in Mathematical Physics*; Springer: Berlin/Heidelberg, Germany, 1994.

27. B. Dragovich, A. Yu. Khrennikov, S. V. Kozyrev, I. V. Volovich, and E. I. Zelenov, p-Adic mathematical physics: The first 30 years, p-Adic Numbers, Ultrametric Anal., Appl. 9, 87-121 (2017).

28. Zelenov, E. I. Entropy gain in p-Adic quantum channels. *Physics of Particles and Nuclei* volume 51, pages 485-488 (2020)

29. Parisi, G. On p-adic functional integrals. *Modern Physics Letters A* 1988, 3(06), 639-643.

30. García-Compeán, H., Edgar Y. López, and W. A. Zúñiga-Galindo. p-Adic open string amplitudes with Chan-Paton factors coupled to a constant B-field. *Nuclear Physics B* 951 (2020): 114904.

31. G Parisi, Infinite number of order parameters for spin-glasses, Physical Review Letters 43(23), 1754 (1979)

32. G Parisi, A sequence of approximated solutions to the SK model for spin glasses, Journal of Physics A: Mathematical and General 13 (4), L115 (1979)

33. G Parisi, The order parameter for spin glasses: a function on the interval 0{1, Journal of Physics A: Mathematical and General 13 (3), 1101 (1979)

34. Parisi, G.; Sourlas, N. P-adic numbers and replica symmetry breaking. *Eur. Phys. J. B Condens. Matter Complex. Syst.* 2000, 14, 535-542.

35. Khrennikov, A. Yu, Kozyrev, S. V. Replica symmetry breaking related to a general ultrametric space I: replica matrices and functionals. *Physica A: Statistical Mechanics and its Applications* 359 (2006), 222-240.

36. Khrennikov A. Yu. Human subconscious as the p-adic dynamical system. J. Theoret. Biol., 193 (1998), 179-196.

37. Albeverio S., Khrennikov A., Kloeden P. E. Memory retrieval as a p-adic dynamical system BioSystems, 49 (1999), pp. 105-115.

38. Dubischar D., Gundlach M., Steinkamp O., Khrennikov A. Yu. A p-adic model for the process of thinking disturbed by physiological and information noise. J. Theoret. Biol., 197 (1999), pp. 451-467.

39. Khrennikov A. (1997). Non-Archimedean Analysis: Quantum Paradoxes, Dynamical Systems and Biological Models, Kluwer Academic Publ., Dordreht.

40. Dragovich B., Dragovich A. A p-adic model of DNA sequence and genetic code. p-Adic Num. Ultrametr. Anal. Appl., 1 (2009), 34-41.

41. Dragovich B., Khrennikov A., Mišić N Ž. Ultrametrics in the genetic code and the genome.

Appl. Math. Comput., 309 (2017), 350-358.

42. Dragovich B, Khrennikov A Y, Kozyrev S V, Mišić N Ž. p-Adic mathematics and theoretical biology. Biosystems. 2021, 199:104288.

43. O. Shor, A. Glik, A. Yaniv-Rosenfeld, Av. Valevski, A. Weizman, A. Khrennikov, F. Benninger EEG p-adic quantum potential accurately identifies depression, schizophrenia and cognitive decline. PLoS ONE 16(8): e025552 (2021).

44. Shor O, Benninger F, Khrennikov A. P-ADIC QUANTUM POTENTIAL IN NEUROPSYCHIATRIC DISEASES 45. Bohm D, Hiley B. J. The Undivided Universe: An Ontological Interpretation of Quantum Theory: Routledge; 1993.

46. Khrennikov, A. (2010b), Ubiquitous Quantum Structure: From Psychology to Finances, Springer, Berlin-Heidelberg-New York.

47. Busemeyer, J. R. and Bruza, P. D. (2012), Quantum Models of Cognition and Decision, Cambridge Press, Cambridge.

48. Asano, M., Khrennikov, A., Ohya, M., Tanaka, Y. and Yamato, I. (2015a), Quantum Adaptivity in Biology: From Genetics to Cognition, Springer, Heidelberg-Berlin-New York.

49. Bagarello F. *Quantum concepts in the social, ecological and biological sciences.* Cambridge University Press, 2019.

50. Birur, B., Kraguljac, N. V., Shelton, R. C., & Lahti, A. C. (2017). Brain structure, function, and neurochemistry in schizophrenia and bipolar disorder-a systematic review of the magnetic resonance neuroimaging literature. *NPJ Schizophr,* 3, 15. doi:10.1038/s41537-017-0013-9

51. Kennis, M., Gerritsen, L., van Dalen, M., Williams, A., Cuijpers, P., & Bockting, C. (2020). Prospective biomarkers of major depressive disorder: a systematic review and meta-analysis. *Mol Psychiatry,* 25(2), 321-338. doi: 10.1038/s41380-019-0585-z 52. Strawbridge, R., Young, A. H., & Cleare, A. J. (2017). Biomarkers for depression-recent insights, current challenges and future prospects. *Neuropsychiatr Dis Treat,* 13, 1245-1262. doi:10.2147/NDT.S114542

53. Zhuo, C., Li, G., Lin, X., Jiang, D., Xu, Y., Tian, H., . . . Song, X. (2019). The rise and fall of MRI studies in major depressive disorder. *Transl Psychiatry,* 9(1), 335. doi:10.1038/s41398-019-0680-6

54. Wu, W., Zhang, Y., Jiang, J., Lucas, M. V., Fonzo, G. A., Rolle, C. E., . . . Etkin, A. (2020). An electroencephalographic signature predicts antidepressant response in major depression. *Nat Biotechnol,* 38(4), 439-447. doi: 10.1038/s41587-019-0397-3.

What is claimed is:

1. A computer implemented method of diagnosing a neuro-psychiatric disorder in a subject, comprising:

receiving a plurality of electroencephalogram (EEG) datasets from a plurality of EEG electrodes monitoring a head of the subject;

dividing the plurality of EEG datasets into a plurality of time intervals, grouping the plurality of EEG datasets divided into time intervals into a plurality of groups, each group including EEG datasets obtained during a common time interval;

for each group:

computing a plurality of events;

wherein each respective event of the plurality of events is computed as at least one of: a vector representation of a respective EEG dataset, and a time interval of a selected length of the respective EEG dataset clustering the plurality of events into a plurality of clusters;

computing a p-adic representation of the plurality of clusters;

extracting a p-adic topology from the p-adic representation of the plurality of clusters;

computing a time series of a plurality of p-adic topologies, each respective p-adic topology computed for each respective group, calculating Euclidean distances between events, of the plurality of events, within each p-adic topology and between events, of the plurality of events, across the p-adic topologies of the time series, computing a personal block dendrogramic holographic signature (PBDHS) value for a subset of events selected from the plurality of events and a subset p-adic topologies selected from the plurality of p-adic topologies according to a first personalized threshold and a second personalized threshold, wherein the first personalized threshold is computed for each respective p-adic topology of the time series, the first personalized threshold separates between a first Euclidean distance between events of the respective p-adic topology and a second Euclidean distance between events of the respective p-adic topology that is smaller than the first Euclidean distance, wherein the first personalized threshold is used to select the subset of events within each respective p-adic topology based on their intra-topology Euclidean distances, wherein the second personalized threshold is computed for all p-adic topologies of the time series, the second personalized threshold separates between a third Euclidean distance between events of across the p-adic topologies of the time series and a fourth Euclidean distance between events of across the p-adic topologies of the time series that is smaller than the third Euclidean distance, wherein the second personalized threshold is used to select the subset of p-adic topologies from the time series based on their inter-topology Euclidean distances, diagnosing the neuro-psychiatric disorder according to the PBDHS value relative to a medical threshold that separates between presence of the neuro-psychiatric disorder and non-presence of the neuro-psychiatric disorder presenting on a display, the PBDHS value and the diagnosed neuro-psychiatric disorder wherein the neuro-psychiatric disorder is selected from the group consisting of: depression, schizophrenia, Alzheimer's disease (AD), and mild cognitive impairment (MCI):

computing a first PBDHS value for the subject prior to administration of a treatment;

according to said diagnosing, treating the subject by administration of the treatment, wherein wherein the treatment is effective for the diagnosed neuro-psychiatric disorder, wherein the treatment is selected from a group consisting of: psychotherapy, anti-depressant medication, anti-psychotic medication, electroconvulsive therapy (ECT), and transcranial magnetic stimulation (TMS);

computing a second PBDHS value for the subject after the the administration of the treatment; and determining a clinically significant response to the treatment that a response to the treatment is clinically significant when the second PBDHS value is statistically significantly different from the first PBDHS value.

2. The computer implemented method of claim 1, wherein the first personalized threshold for a respective p-adic topology, of the plurality of p-adic topologies, is computed as being lower than a maximal p-adic ball of the respective p-adic topology by a first parameter fixed at a same value for the other p-adic topologies of other subjects.

3. The computer implemented method of claim 1, wherein the second personalized threshold for a respective p-adic topology all p-adic topologies of the time series, is computed as being lower than a maximal p-adic ball of the p-adic topologies of the time series by a second parameter, wherein the second parameter is fixed at a same value for the other p-adic topologies of other subjects.

4. The computer implemented method of claim 1, wherein the p-adic representation comprises a dendrogram, wherein each branch of the dendrogram represents a respective event, of the plurality of events.

5. The computer implemented method of claim 4, wherein the dendrogram comprises a homogenous tree with a same number of edges for each vertex, wherein each vertex includes one incoming edge and two outgoing edges.

6. The computer implemented method of claim 5, wherein each branch of the dendrogram is labeled by a binary number denoting a natural number encoding each respective branch, wherein a set of all branches is a 2D structure denoting the p-adic representation of the dendrogram, wherein the p-adic representation of the dendrogram encodes relations of each respective branch to all other branches, wherein a Euclidean distance between the natural numbers encoding each respective branch is denoted by a common root-branch, wherein a longer common root indicates a shorter Euclidean distance.

7. The computer implemented method of claim 1, wherein the p-adic representation indicates relative and non-absolute relationships between the events.

8. The computer implemented method of claim 1, further comprising computing a plurality of second Euclidean distances, each respective second Euclidean distance computed for a respective pair of the plurality of EEG datasets, wherein the clustering comprises computing a hierarchical relationship between the plurality of second Euclidean distances, wherein the p-adic representation is computed according to the hierarchical relationship.

9. The computer implemented method of claim 1, wherein the first personalized threshold and the second personalized threshold is are computed as being lower than a maximal p-adic ball of the respective p-adic topology and lower than a maximal p-adic ball of all the p-adic topologies of the time series respectively by a parameter, wherein the parameter is fixed at a same value for other subjects.

10. The computer implemented method of claim 1, wherein the first personalized threshold and the second personalized threshold are computed individually for each subject, and vary between subjects according to the respective p-adic topology topologies of the respective subject.

11. The computer implemented method of claim 1, wherein the medical threshold that separates between presence of the neuro-psychiatric disorder and non-presence of the neuro-psychiatric disorder is set by:

computing a plurality of PBDHS values, each PBDHS value for associated with one of a plurality of subjects associated with an indication of presence the neuro-psychiatric disorder or an indication of non-presence of the neuro-psychiatric disorder, using respective EEG datasets; and setting the medical threshold to separate between PBDHS values of subjects associated with the indication of presence the neuro-psychiatric disorder, and PBDHS values of subjects associated with the indication of non-presence of the neuro-psychiatric disorder.

12. The computer implemented method of claim 1, wherein p-adic comprises 2-adic.

13. The computer implemented method of claim 1, wherein the non-presence of the neuro-psychiatric disorder is selected from the group consisting of: no neuro-psychiatric disorder, and another neuro-psychiatric disorder that is different from the diagnosed neuro-psychiatric disorder.

14. The computer implemented method of claim 1, wherein the presence of the neuro-psychiatric disorder comprises AD or MCI and is further selected from the group consisting of: stable AD, stable MCI and the non presence of the neuro-psychiatric disorder is selected from the group consisting of: deteriorating AD, and deteriorating MCI.

15. The computer implemented method of claim 1, wherein the presence of the neuro-psychiatric disorder further comprises a prediction of likelihood of developing the neuro-psychiatric disorder in the future, and the non-presence of the neuro-psychiatric disorder further comprises a prediction of likelihood of not developing the neuro-psychiatric disorder in the future.

16. The computer implemented method of claim 1, wherein the presence of the neuro-psychiatric disorder further comprises a prediction of likelihood of positively clinically significantly responding to a certain treatment for the neuro-psychiatric disorder, and the non-presence of the neuro-psychiatric disorder further comprises a prediction of likelihood of no clinically significant response to the certain treatment for the neuro-psychiatric disorder.

\* \* \* \* \*